United States Patent
Rizwan

(10) Patent No.: US 9,161,693 B2
(45) Date of Patent: Oct. 20, 2015

(54) MINIATURIZED ELECTRONIC DEVICE INGESTIBLE BY A SUBJECT OR IMPLANTABLE INSIDE A BODY OF THE SUBJECT

(75) Inventor: Bashirullah Rizwan, Gainesville, FL (US)

(73) Assignee: University of Florida Research Foundation, Inc., Gainsville, FL (US)

( * ) Notice: Subject to any disclaimer, the term of this patent is extended or adjusted under 35 U.S.C. 154(b) by 636 days.

(21) Appl. No.: 13/257,151

(22) PCT Filed: Mar. 18, 2010

(86) PCT No.: PCT/US2010/027773
§ 371 (c)(1),
(2), (4) Date: Sep. 16, 2011

(87) PCT Pub. No.: WO2010/107980
PCT Pub. Date: Sep. 23, 2010

(65) Prior Publication Data
US 2012/0008714 A1   Jan. 12, 2012

Related U.S. Application Data

(60) Provisional application No. 61/161,441, filed on Mar. 19, 2009.

(51) Int. Cl.
*H04W 88/02* (2009.01)
*A61B 5/00* (2006.01)

(52) U.S. Cl.
CPC ............. *A61B 5/0031* (2013.01); *A61B 5/0028* (2013.01); *A61B 2560/0219* (2013.01)

(58) Field of Classification Search
CPC .............. A61N 1/3785; A61B 5/0002–5/0031
USPC .......... 340/573.1–573.7; 607/32, 35; 128/899
See application file for complete search history.

(56) References Cited

U.S. PATENT DOCUMENTS

| | | | |
|---|---|---|---|
| 4,987,897 A * | 1/1991 | Funke | 607/32 |
| 5,626,630 A * | 5/1997 | Markowitz et al. | 607/60 |
| 5,970,986 A * | 10/1999 | Bolz et al. | 128/899 |
| 6,456,883 B1 * | 9/2002 | Torgerson et al. | 607/34 |

(Continued)

OTHER PUBLICATIONS

PCT International Search Report dated Nov. 9, 2010 for International Application No. PCT/US2010/027773 filed on Mar. 18, 2010.

*Primary Examiner* — Catherine B Kuhlman
(74) *Attorney, Agent, or Firm* — Allen Dyer Doppelt Milbrath & Gilchrist

(57) ABSTRACT

A miniaturized in-body electronic device is provided. One or more antennas (e.g., 32) may be galvanically coupled to receive an alternating current (AC) signal through the body of a subject where the in-body electronic device is located. Power extraction circuitry (e.g., 36) is configured to extract electrical power from the AC signal received by the antenna. The extracted electrical power is used for electrically powering one or more components of the electronic device. A transmitter (e.g., 48) is coupled to receive power from the power extraction circuitry. A controller (e.g., 46) is coupled to the transmitter. The controller is configured to activate the transmitter to generate a sequence of intermittent transmission bursts for transmitting an uplink signal. A transmission burst may have a higher instantaneous power level than an instantaneous power level of the AC signal received by the antenna.

12 Claims, 21 Drawing Sheets

(56) References Cited

U.S. PATENT DOCUMENTS

| | | | |
|---|---|---|---|
| 6,622,567 B1* | 9/2003 | Hamel et al. | 73/786 |
| 6,700,491 B2* | 3/2004 | Shafer | 340/572.7 |
| 8,032,227 B2* | 10/2011 | Parramon et al. | 607/61 |
| 2003/0045913 A1 | 3/2003 | Stroebel et al. | |
| 2003/0229382 A1* | 12/2003 | Sun et al. | 607/60 |
| 2005/0099290 A1 | 5/2005 | Govari | |
| 2007/0123772 A1 | 5/2007 | Euliano | |
| 2007/0228273 A1* | 10/2007 | Sun et al. | 250/305 |
| 2008/0033502 A1 | 2/2008 | Harris et al. | |
| 2008/0306360 A1* | 12/2008 | Robertson et al. | 600/302 |

\* cited by examiner

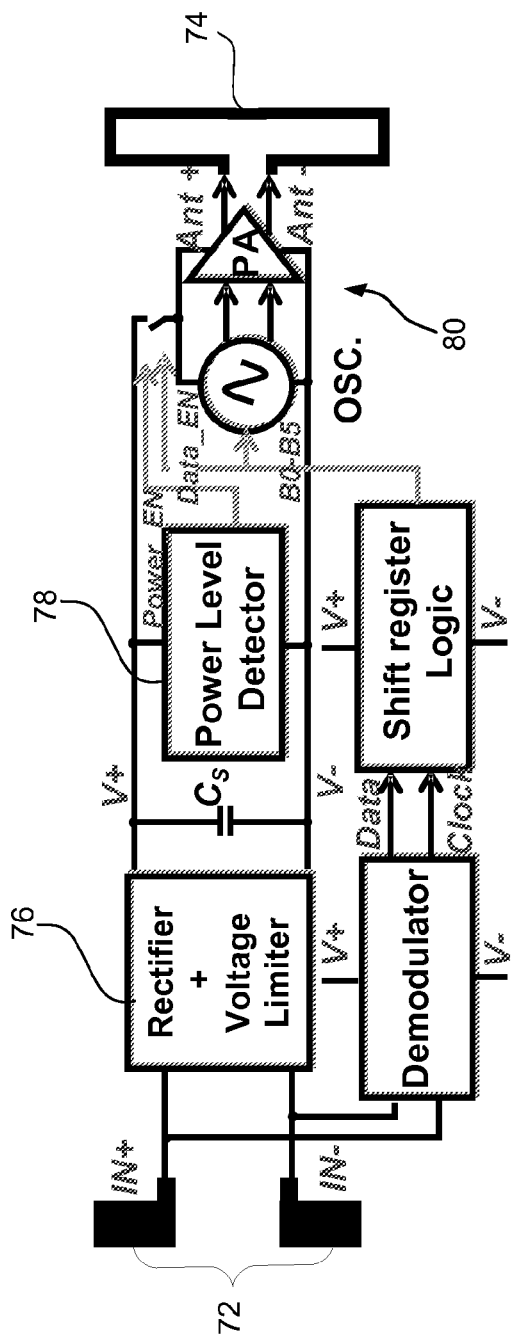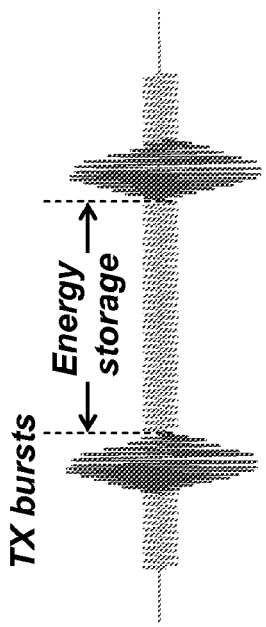
FIG. 7

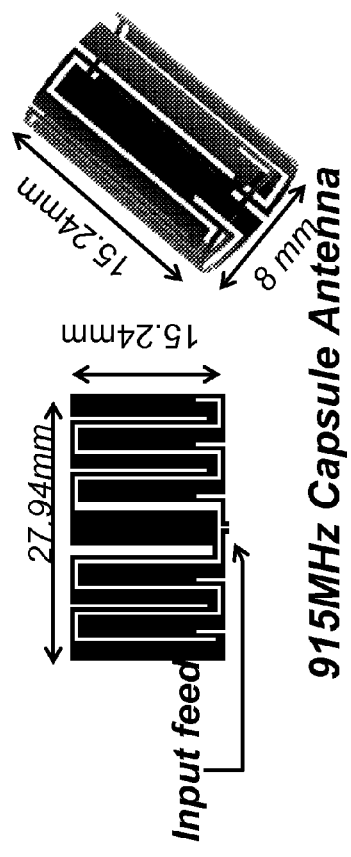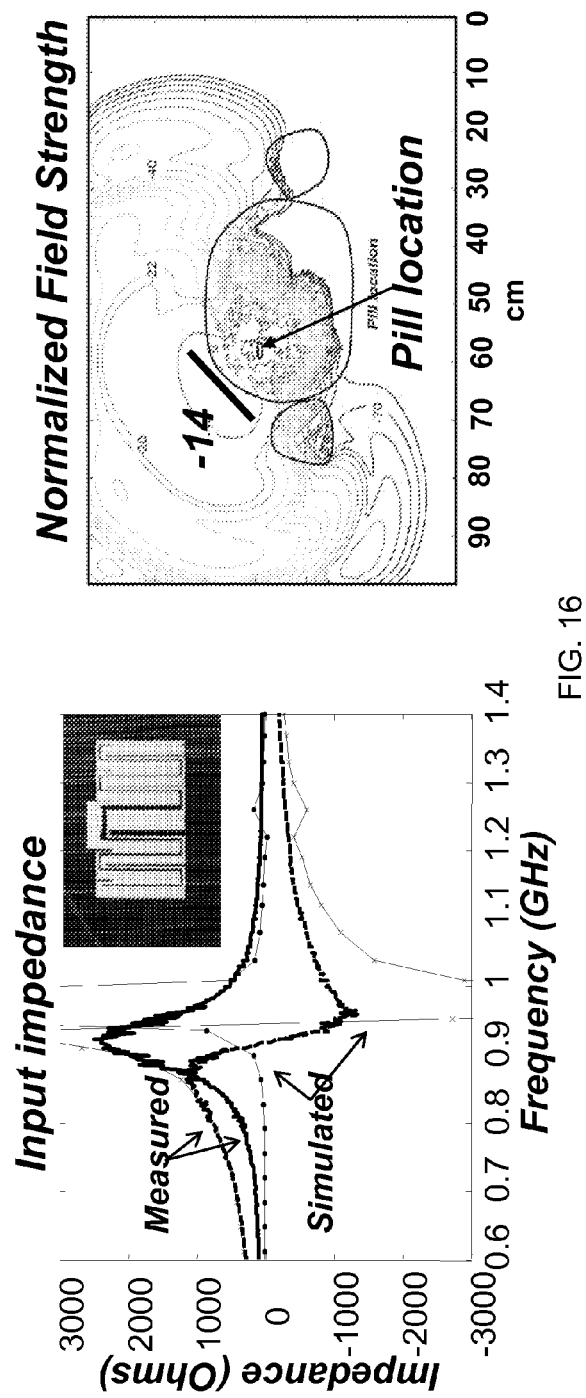
FIG. 16

MINIATURIZED ELECTRONIC DEVICE INGESTIBLE BY A SUBJECT OR IMPLANTABLE INSIDE A BODY OF THE SUBJECT

RELATED APPLICATIONS

This application is the §371 National Stage of International Application No. PCT/US2010/27773, filed on Mar. 18, 2010, which claims the benefit of U.S. Provisional Application Ser. No. 61/161,441, filed on Mar. 19, 2009, under 35 USC §119 (e), which are incorporated herein by reference in their entirety.

STATEMENT REGARDING FEDERALLY-SPONSORED RESEARCH OR DEVELOPMENT

This invention was made with Government support under Grant IIP-0646491 awarded by the National Science Foundation. The Government has certain rights in the invention.

FIELD OF INVENTION

The present invention is generally related to in-body electronic devices, and, more particularly, to techniques and circuits for powering and communicating by way of miniaturized electronic devices inside humans or animals.

BACKGROUND OF INVENTION

Medication compliance is the degree to which a medication is taken according to a prescribed treatment and is usually measured in terms of percent of doses taken over a given interval. It is estimated that thousands of people may die of treatable ailments because of poor adherence and a tenth of hospital admissions are associated with noncompliance at a healthcare services expense of approximately $15.2 billion annually. Medication compliance is also important in the context of clinical drug trials, geriatrics, and mental health/addiction medicine. For example, in a clinical drug trial it is desirable to know, with a high degree of certainty, the patient's compliance to a medication regimen, because without such knowledge the results from a clinical trial cannot be accurately interpreted or could even be misleading. In each case there is a clear and present need for relatively low-cost, automated technologies that can replace directly observed therapy (DOT), which is one known method of determining medication compliance. This known method tends to be costly and cumbersome since it depends on human labor.

An orally ingestible pill with an embedded passive microsystem disposed of via the gastrointestinal (GI)-tract and capable of communicating with devices external to the body can lead to an improved indirect method for monitoring a patient's adherence to a regimen. The current state of the art in passive microsystems for in-body communications does not fully address the fundamental challenges associated with severe signal attenuation inside human tissues, poor radiation properties of electrically small antennas, limited power for signaling and high path loss dependence on distance.

Known approaches utilize devices which are predominantly battery powered as at large distances the transmitted signals are severely attenuated inside the human body (i.e. the signal attenuation depends on various factors such as frequency of operation, tissue attenuation, electrical antenna size, mismatch losses, etc). Since batteries ultimately limit the potential for miniaturization (i.e. silicon devices can be orders of magnitude smaller), aspects of the present invention focus on passive microsystems. It will be appreciated, however, that the techniques described herein may also be applicable to battery powered systems.

In the context of passive devices, the operational range of biomedical devices inside the body is substantially limited (e.g., typically a few cm due to weak coupling, high tissue attenuation and/or human exposure limits to radio frequency (RF) fields). Traditional passive radio-frequency identification (RFID) transponders operating in the far-field suffer from space/frequency tradeoffs not suitable for miniaturized in-body communication. Since electrically large antennas in the far-field of operation are required to capture sufficient RF power to activate the transponder, devices with small antennas when operated at low frequencies suffer from poor radiation characteristics and when operated at high frequencies suffer from increased signal attenuation. Near-field transponders powered from low frequency magnetic fields have limited range, require multi-turn coils which are often wrapped around ferrite core materials to improve signal coupling, and suffer from power/bandwidth/size tradeoffs.

BRIEF DESCRIPTION OF INVENTION

Aspects of the present invention include a low power electronic RF tagging device, such as in one example application may be used for medication compliance monitoring. However, aspects of the present invention are not limited to medication compliance applications. For instance, the technology described herein can be used to tag chronic implants such as biomedical devices, bones and organs as a means to track surgical procedures while providing valuable patient information. The microchip may also be attached to surgical tools used in the operating room and scanned after surgery to ensure items are not inadvertently left inside the body.

Example embodiments contemplated by aspects of the present invention may include an apparatus and method of powering and communicating by way of miniaturized electronic devices, which are ingested or implanted in humans or animals for the purpose of detecting the presence of an object or enabling functional tasks such as sensing or stimulating biological tissues. It is contemplated that for powering an in-body communication passive device one may use power conditioning circuits to scavenge energy from either weak incident electromagnetic fields and/or from internal electrical sources generated by internal biological electrochemical gradients, and subsequently transmitting data in bursts to achieve higher power levels than what would be possible using conventional methods such as backscattering.

Further aspects of the invention include a method of powering and communication for miniaturized passive electronic implants. One proposed concept is referred to in this description as an Electronic Burst or E-burst signaling apparatus. The E-burst device may communicate using primarily magnetic (e.g., inductive), primarily electric (e.g., capacitive), electromagnetic signals, and/or galvanic signaling using the human body as an electrical transmission medium. A preferred modality of operation is to use galvanic coupling to power the electronic microchip. This modality may utilize external electrodes in direct contact with the skin to create an alternating voltage, which in turn generates an alternating current transmitted through the human body. The current flows through the human body as conductive medium to induce a differential voltage across input ports of the microchip. The voltage can be captured using two pads or electrodes, which may or may not be exposed to internal conductive tissue and body fluids. This powering modality does not require a line of site or carefully aligned coils, such as in the case of inductively coupled implants. Thus, one can envision powering an ingested or implanted microchip using an arm band transmitter, a watch, a handheld phone or personal digital assistant (PDA).

In yet further aspects of the present invention, the device extracts energy from the differential voltage generated across receiving pads and/or antenna. The proposed E-burst device may signal back to a reader after storing a sufficient amount of energy to generate signal bursts greater than the instantaneous power levels induced across the input terminals. That is, the device is able to generate power levels across the output antenna relatively higher than the captured power. Using this technique, the device is able to generate externally detectable bursts and circumvent the high tissue attenuation associated with the human body. The overall E-burst concept is different from current state-of-the-art communication devices used in biomedical systems which generally require on-board battery sources to power the device. By way of comparison, passive (or battery-less) systems, such as RFID tags and transponders communicate by means of backscattering, generating at best only a fraction the power that is incident across the antenna ports, thereby limiting the detection range.

A single or multiple antennas may be used as radiating elements for communicating with external detectors. Moreover, antennas may be entirely embedded within the microchip to establish powering and communication protocols with the external reader. In addition, the tagging device may use one or two frequencies to power and communicate with the external reader. The choice of frequency can be optimized independently for powering and communications. For instance, one may choose to power the device at lower frequencies using galvanic signal coupling, as the signal attenuation inside the body may be relatively low; and the communication from the tag to the reader may be established using a higher frequency carrier using either near field or far-field coupling to improve the efficiency of the transmitting antenna and increase the signal transmission data rates.

In another example embodiment, referred to as a supply modulated tag, galvanic coupling is used to create a differential potential across the receiving electrodes. The device can be made to function without the use of a rectifier to generate bursts of RF energy at higher frequency. In this example embodiment, the internal circuits operate from a supply voltage that varies over time, such as an alternating current (AC) modulated supply. The device generates bursts when the differential voltage across the input ports of chip exceeds the minimum threshold to active the internal electronics. The circuitry is designed to function properly in the presence of a varying supply voltage.

The following description presents as an example an RF capsule tagging device, such as may be used for medication compliance monitoring, which uses antennas or electrodes to capture the induced voltage and transmit signals to an external reader. Antennas can be made of conductive bio-compatible coatings by incorporating a metal, which can dissolve, such as silver, under a temporary protective layer such as polyglycolic acid, or by incorporating particles that are non-toxic by virtue of being non-absorbable. Thus, the substrate for the antenna can be attached to the drug delivery device and the volume reserved for the medication remains unchanged. The medication capsule can therefore house on its outer surface an electronic compliance device. The RF tagging IC in this system-on-a-capsule can be made thin, mechanically compliant and small under a biocompatible protective sealant and excreted via the GI track.

The features that characterize aspects of the present invention will be better understood from the following description used in conjunction with the accompanying drawings. It is to be expressly understood that the drawing is for the purpose of illustration and description and is not intended as a definition of the limits of the invention.

BRIEF DESCRIPTION OF DRAWINGS

FIG. 7 shows a block diagram of example circuit architecture of a proposed RF tagging device, or Electronic Burst (E-burst) device 70.

FIG. 16 shows an example embodiment of a 915 MHz antenna configured to wrap around an ingestible capsule.

DETAILED DESCRIPTION OF THE INVENTION

In the following description of example embodiments, reference is made to accompanying drawings which are used to facilitate an understanding of aspects of the present invention.

Figure 1:
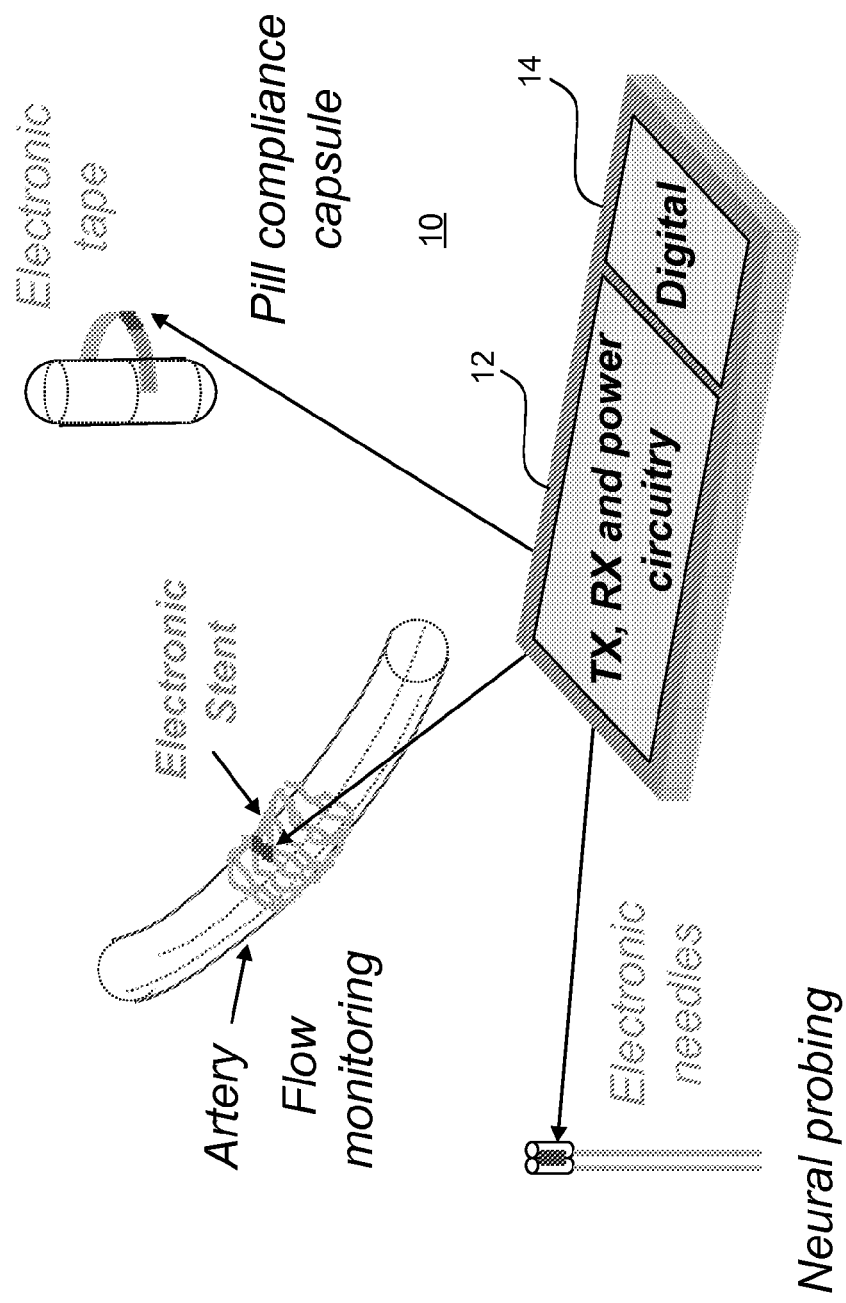
FIG. 1 shows a schematic of an example miniaturized micro-electronic system that may benefit from aspects of the present invention.

FIG. 1 is a schematic of an example passive micro-electronic system 10 that may benefit from aspects of the present invention. System 10, as may be manufactured using standard semiconductor processing such as complementary metal oxide semiconductor (CMOS) or any other suitable integrated circuit (IC) technology. The micro-electronic system may comprise a transceiver 12, a digital processor 14, and/or IC-compatible sensors, such as may be used for monitoring one or more parameters, such as pH level, temperature, oxygen levels, etc. The system, as may be constructed on an IC chip, is highly miniaturized so that it virtually invisible to the human eye, and may be inexpensively produced so that it can be fabricated in large numbers for high-volume applications (e.g., electronic pills, electronic stents, electronic needles). A radio frequency (RF) subsystem portion of the system 10 may include a general purpose RF sensor system that can be used to perform multiple functions depending on the available on-chip support circuitry. Groups of passive microsystems can be used to form in-body communication networks to monitor a variety of body functions.

Figure 2:
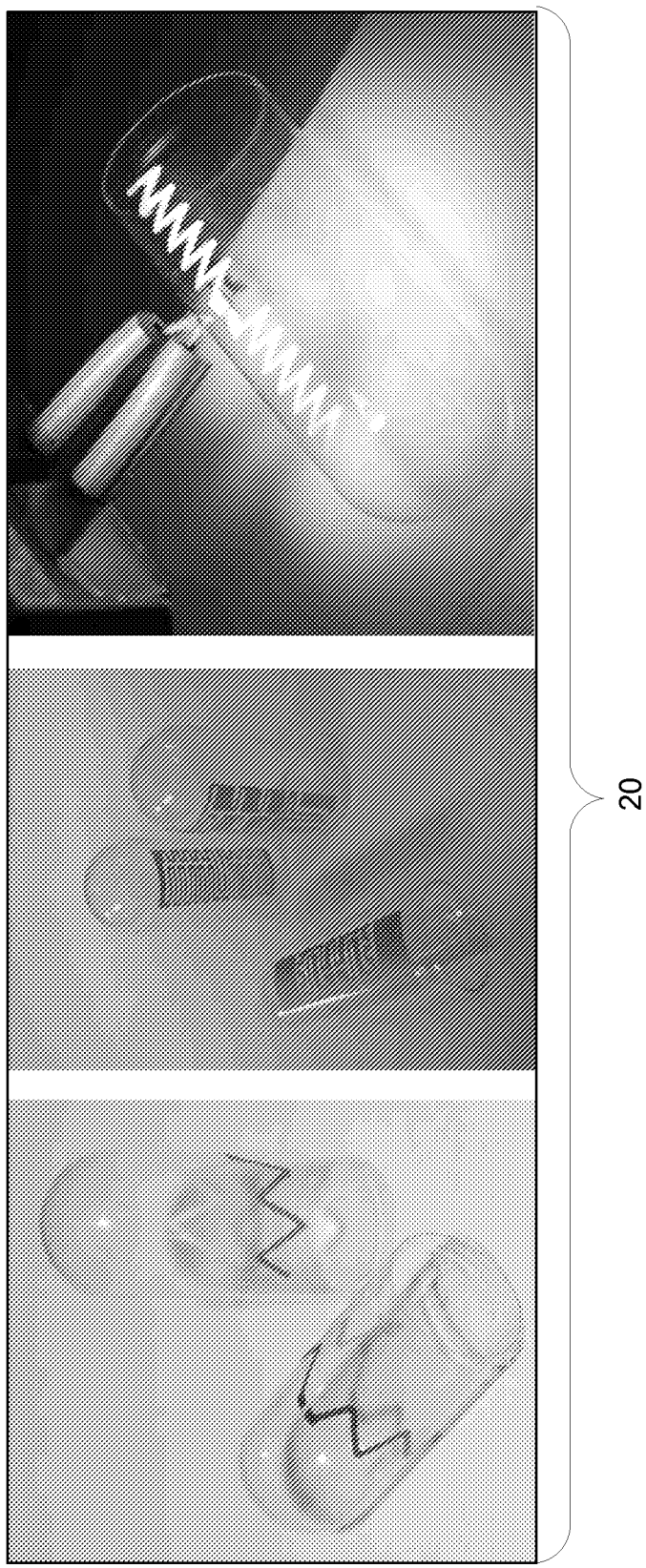
FIG. 2 illustrates example printed antennas as may be attached onto respective surfaces of ingestible capsules.

Antennas of various shapes and sizes can be attached to conform to a desired volume (i.e. a thin tape, capsules, artery stent, needle or a suturing wire may all be configured as antennas). Respective examples of printed antennas 20 as may be disposed directly onto the surface of ingestible capsules are shown in FIG. 2. Antennas of various shapes and sizes can be attached to conform to a desired volume (e.g., a thin tape, capsules, artery stent, needle or a suturing wire can all be antennas). Antennas 20 could also be made of conductive bio-compatible coatings by incorporating a metal, which can dissolve, such as iron, under a temporary protective layer such as polyglycolic acid, or by incorporating particles that are non-toxic by virtue of being non-absorbable (i.e. silver or carbon). Antennas can be printed directly on engineered substrates which dissolve in water or when exposed to solutions with specific pH levels. A single or multiple antennas may be used and attached via standard methods to electronic devices.

Figure 3:
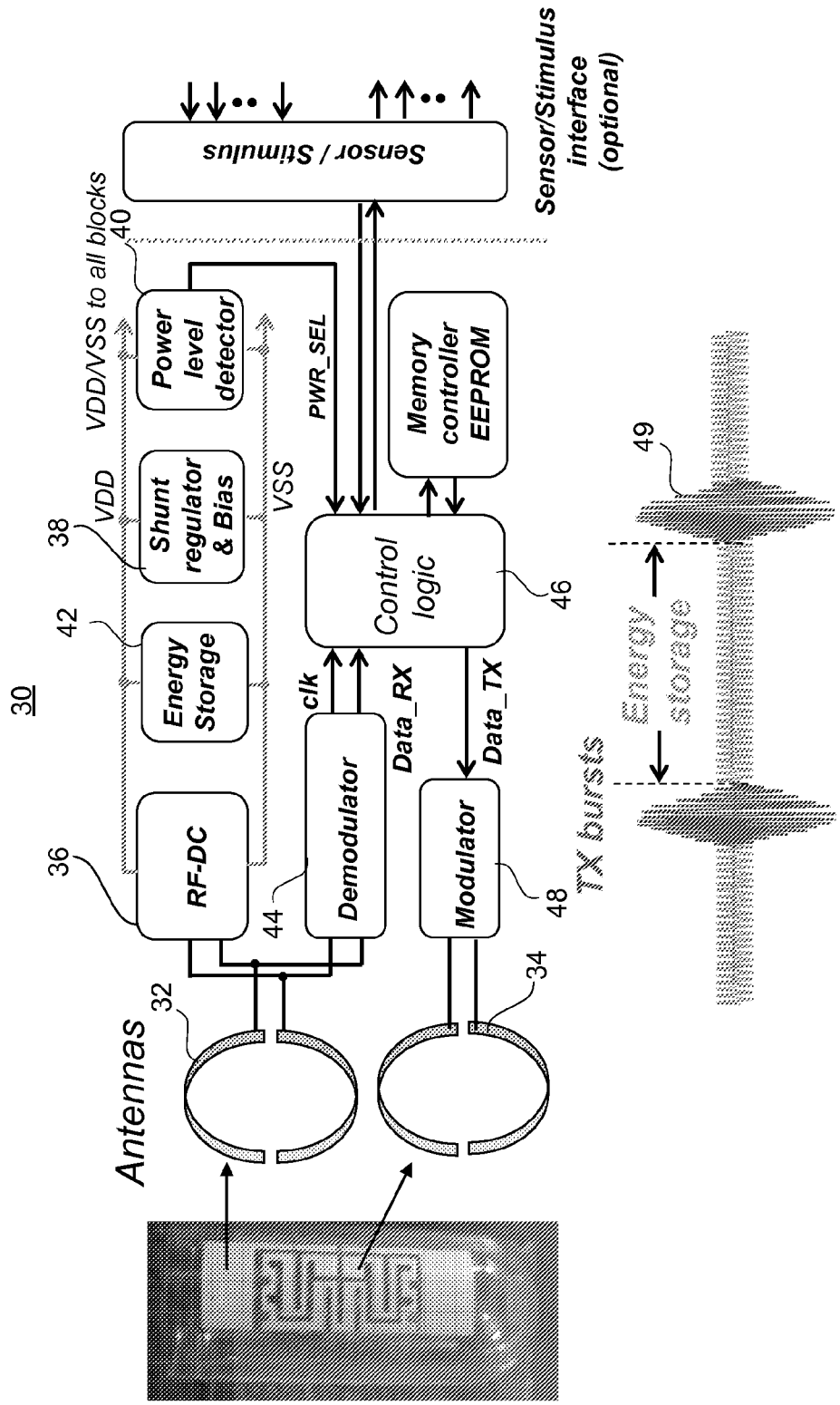
FIG. 3 shows a block diagram of one example embodiment of an in-body communication signaling device embodying aspects of the present invention and including example waveforms representative of transmission burst transmitted by the device.

FIG. 3 shows an example embodiment of an in-body communication E-burst signaling device 30 embodying aspects of the present invention. In this example embodiment, signaling device 30 comprises two antennas 32 and 34, one for receiving power and data (e.g., antenna 32) and the other for transmitting data (e.g., antenna 34). Devices embodying aspects of the present invention may preferably operate by storing energy captured via a power link (e.g., a galvanic power link) and then transmitting (e.g., bursting) pulses at power levels higher than the incident power. See example waveforms 49 representative of transmission burst transmitted by the device. The energy may be captured by one or more antennas, one or more contact pads, which may or not be exposed. That is, such antennas or pads could be constructed external to the device or could be constructed within the device, (e.g., embedded in the chip).

The receiving antenna 32 functions as an input port to incident electric fields and can be operated in a near or a far field mode. The incident signals in the near-field can be primarily magnetic or capacitive or galvanic (using the human body as a conduction medium). The antennas can also be designed for far-field operation to support electromagnetic RF signals. Power extraction circuitry, such as may include an RF-to-DC converter 36 to extract a direct current (DC) to power all on-board electronic circuits. A power conditioning circuit 38 provides appropriate conditioning to power supplied by RF-DC converter 36 and a power level detector 40 monitors the power supplied by the RF-DC converter. At least some of the power supplied by RF-DC converter may be stored in an on-chip energy storage element 42.

A demodulator circuit 44 may be used to extract data from a modulated RF carrier. Standard modulation techniques, such as amplitude shift keying (ASK) or phase shift keying (PSK), may be used in combination with pulse position or pulse width modulation schemes. The information extracted by the demodulator may be supplied to an on-board controller 46 to update device settings, which may be stored using programmable memory elements, such as flash memory cells. The on-board controller also monitors the output of the power level detector and activates a transmitter when the appropriate command from an external reader is received and when the stored power level reaches a desired threshold. The desired threshold may be user programmable. The transmitter may consist of a modulator 48 (e.g., oscillator) connected directly to the output port antenna 34. The reactive impedance of the antenna and on-chip digitally controlled capacitive tuning elements may be used to set a desired operating frequency.

Figure 4:
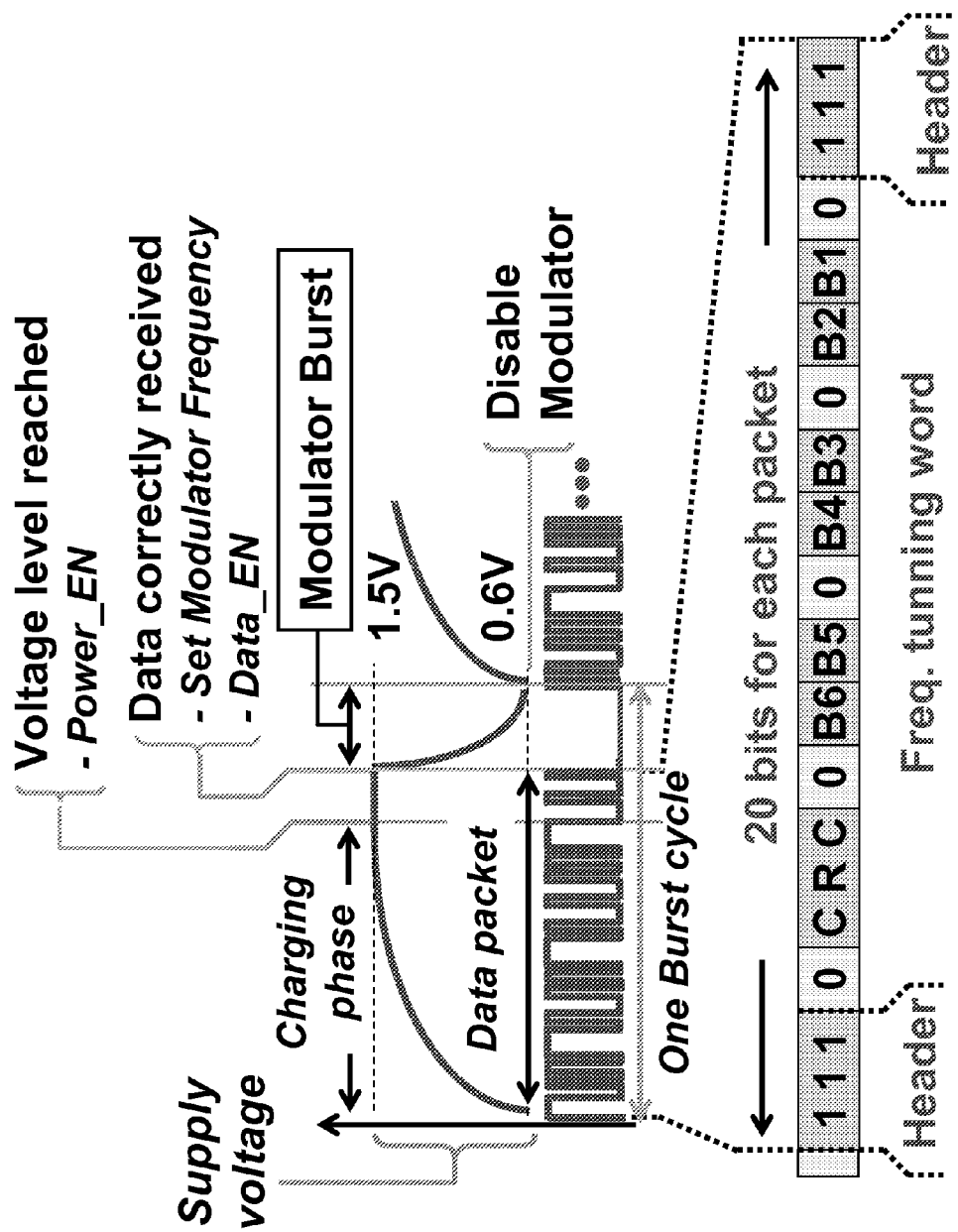
FIG. 4 shows an example timing diagram in connection with transmission of data packets from a signaling device embodying aspects of the present invention.

The transmitter may be activated to transmit a stream of data packets, as shown in the example timing diagram shown in FIG. 4. The transmitter activation may occur either while the input port continues to receive signals from an external RF carrier or in the absence of such external carrier. The latter operation decreases the amount of interface for the external reader or detector. The input and output ports may be operated at the same frequency or at two different frequencies. The input and output may use a single antenna or two antennas. The latter operation provides improved signal isolation. For example, the input port may use a low-frequency near-field antenna whereas the output port transmitting antenna may use a far-field antenna. Similarly, the low frequency antennas may be viewed as coupling electrodes to capture an alternating potential difference generated from current flow through the body. In this case, the ionic fluid within the human body serves as a conduction medium. Signals to the input port of the electronic device may be supplied using external electrodes in direct contact with the skin or via a near field external antenna element. Feed electrodes can be placed in direct contact with the skin in relatively close proximity to generate a differential voltage which in turn generates alternating currents. The current flows primarily between the feed electrodes, while secondary currents flow into the human body to generate a differential voltage across the receiver electrodes. The alternating currents can be modulated to establish digital or analog communication protocols to and from the electronic device.

Figure 5:
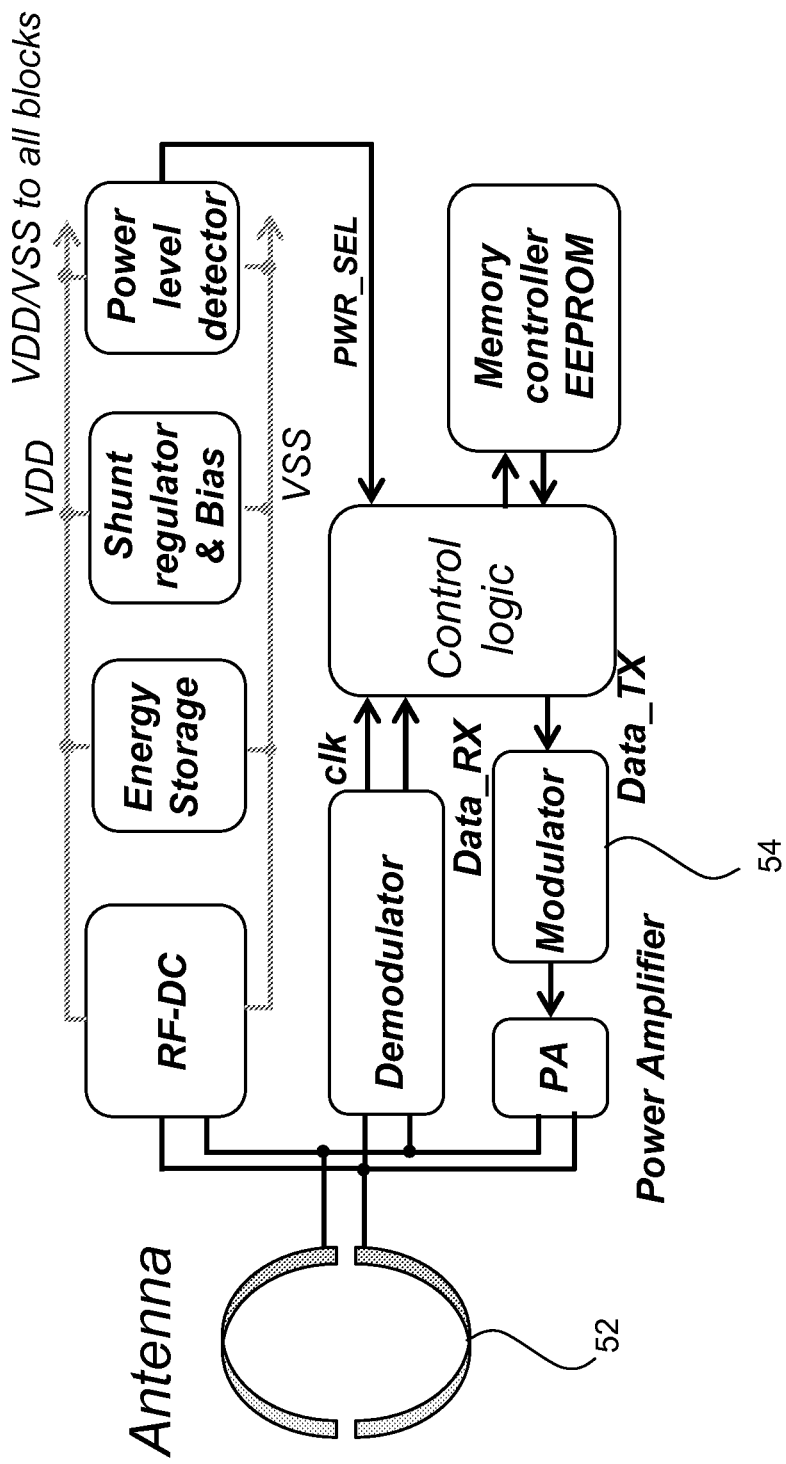
FIG. 5 shows a block diagram of another example embodiment of an in-body signaling device embodying aspect of the present invention.

FIG. 5 shows another example embodiment of an E-burst signaling device 50 embodying aspect of the present invention. This example embodiment utilizes a single antenna 52. In this embodiment, the transmitter may superimpose its signal on the receiving signal or transmit in the absence of an input signal. The latter operation provides time division between receive and transmit signals for improved isolation at the external reader. The transmitter may also use backscattering to communicate with external detectors. The transmitter may communicate with the external reader using magnetic, capacitive or galvanic signal transmission. A power amplifier PA may be optionally coupled between the antenna 52 and the on-chip modulator 54 (e.g., oscillator) to increase the transmission power level and improve signal isolation between receive and transmit paths. Circuitry as described in the context of device 30 may be similarly used in this embodiment, such as RF-DC converter, power conditioning circuit and power level detector.

Figure 6:
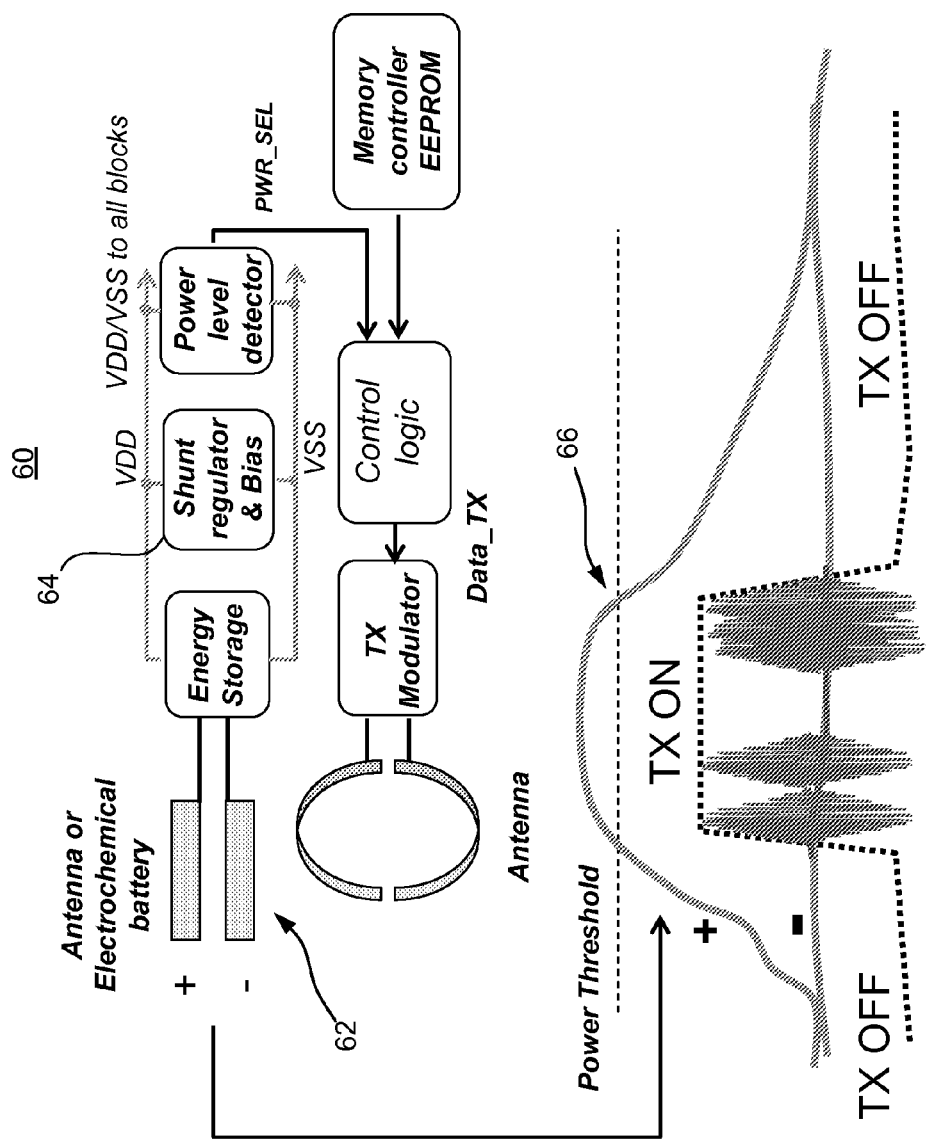
FIG. 6 shows a block diagram of yet another example embodiment of a signaling device embodying aspect of the present invention and including example waveforms indicative of transmission burst transmitted by the device.

FIG. 6 shows an example embodiment of an E-burst device 60, which eliminates from the power extraction circuitry the RF-DC converter. In this example embodiment, the transmitter may be powered directly from relatively low frequency incident fields across its input port 62. The on-board transmitter is activated when the differential voltage induced across the input port exceeds a threshold set by the required voltage margins of the device or by a predefined threshold of a power conditioning circuit 64. See example waveforms 66 representative of transmission bursts transmitted by the device. Note that there is no bursting when the value of the voltage differential is below the threshold value. The voltage across the input port may be generated from low frequency externally induced signals or by power sources generated by internal electrochemical gradients. The voltage profile and shape across the input port may be a periodic sinusoidal signal or any other shape with an electrical potential that is sufficiently large to power the device. Electrochemical reactions using internal gastric acid and oxidizing and reduction electrodes which are patterned onto ingestible objects, such as pills may also be used to supply power for the E-burst device. The voltage induced across the input port may appear as a single-shot timing event to activate the transmitter when the ingestible object comes in contact with stomach acid or other substances in the digestive system with the appropriate pH level.

It will be appreciated that an RF-DC multiplier could be used in conjunction with an internal electrochemical battery to improve the communication range and sensitivity of device 60. The internal device or tag may be designed to use multiple power sources (electrochemical battery, galvanic currents, capacitive or magnetic fields). Voltages generated by electrochemical reactions may also be used in conjunction with each of the above embodiments described herein as a means to, for example, signal the presence of an ingestible object in the digestive system. This technique may be used to identify the origin of the electronic signal transmission.

In operation an electronic device embodying aspects of the present invention can be powered from weak incident RF fields (electromagnetic, magnetic, capacitive or galvanic) or by means of internal electrical sources generated by the body's own electrochemical gradients (e.g., muscular, digestive and/or neural activity at the intercellular and/or organ levels). The device may contain dissolvable materials such as biocompatible antennas or electrodes that enable one-time or continuous communication with external user controlled scanning systems. A single or multiple radiating elements, and one or multiple frequencies in the near or far field of operation may be used to power, receive and transmit data to external detectors. The device may communicate with external detectors by modulating instantaneous incident fields or by storing energy and subsequently transmitting information in bursts. The transmitted power levels may be less or exceed the instantaneous received power used to activate the electronic device.

Below are described two example devices that use asymmetric RF tagging architectures conducive to circumvent problems associated with signal attenuation inside the human body and poor radiation efficiency of electrically small antennas. The example devices may be powered by low frequency AC signals via galvanic coupling to create externally detectable RF bursts at higher frequencies, for example. Prototype test RFICs were fabricated in 130 nm CMOS technology and experimentally validated inside a phantom solution to mimic signal propagation inside a human torso.

E-BURST

Figure 8:
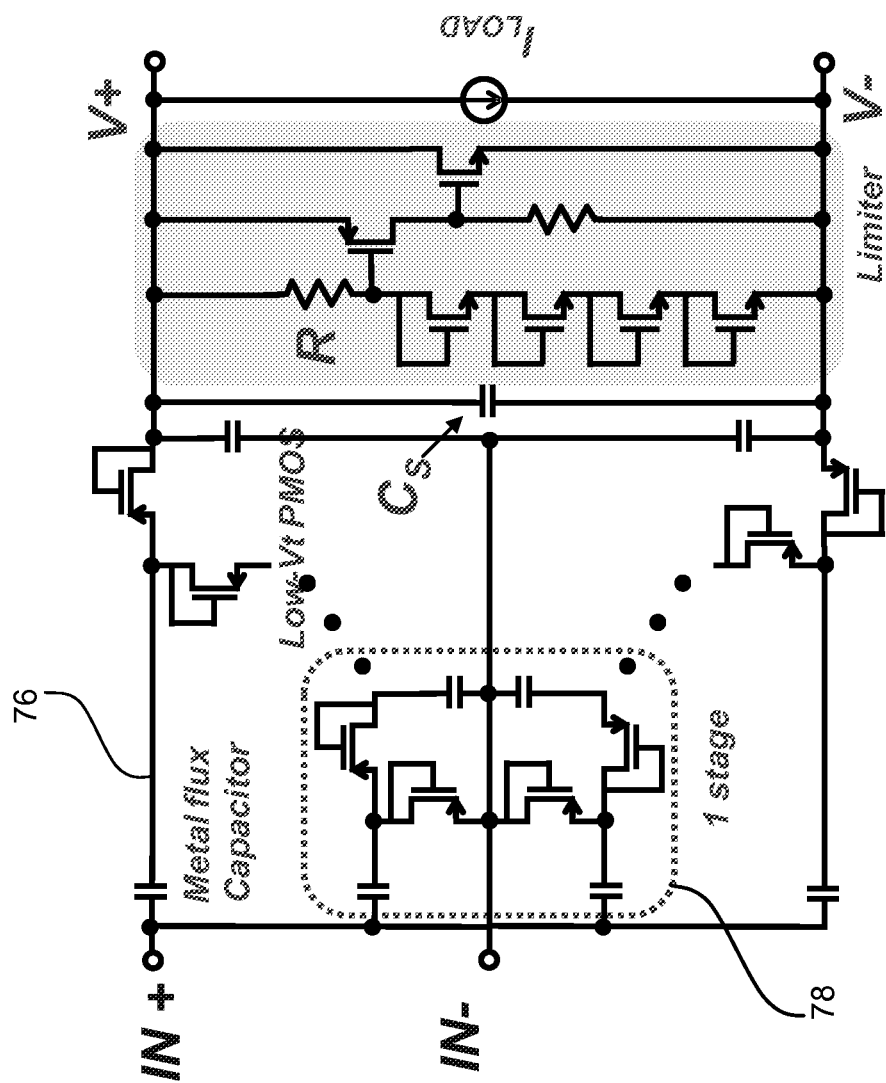
FIG. 8 shows a multistage RF rectifier as may be used by circuitry embodying aspects of the present invention.

FIG. 7 shows a block diagram of example circuit architecture of a proposed RF tagging device, or Electronic Burst (E-burst) signaling device 70. This example embodiment uses two antennas in the form of a pair of low frequency pads 72 to energize the microchip and provide downlink command functions; and a higher frequency antenna 74 used for uplink to an external detector. In other example embodiments of the proposed device, a single antenna may also be used for powering and communication functions. In addition, a single frequency or multiple frequencies may be used to establish these functions. An input RF rectifier 76, such as may comprise a number of differential RF-DC converter stages 78 (FIG. 8), powers the device from a signal having a frequency, such as 13.56 MHz. The rectifier supplies current to a storage capacitor $C_s$ until the supply voltage exceeds a programmed value set by a power level detector 78. The power detector is used to monitor the storage capacitor voltage and signals the device ready for transmission. An output transmitter 80 generates short bursts at approximately 915 MHz when both the power level and appropriate downlink data has been received. The frequency of the RF burst may be controlled by a 6-bit digital word programmed by the user via a downlink data stream. A 3-bit cyclic-redundancy-check (CRC) code may be used for data integrity and the TX burst may be generated only after the CRC has been verified.

Figure 9:
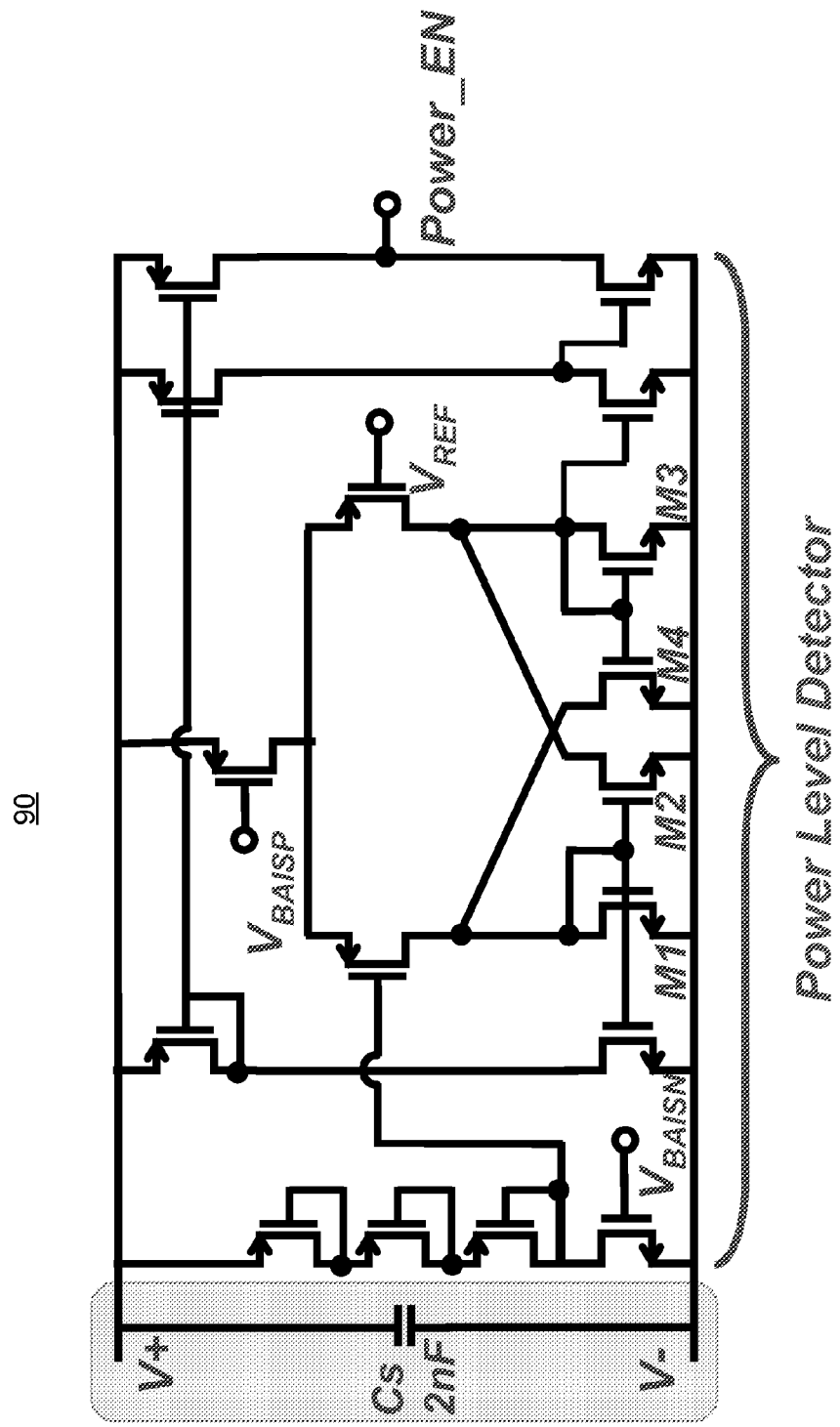
FIG. 9 shows a block diagram of an example of a power level detector as may be used by circuitry embodying aspects of the present invention.

FIG. 9 shows a block diagram of an example embodiment of a power level detector 90, as may be used to continuously monitor the voltage across storage capacitor Cs. When the voltage across the capacitor is higher than a predetermined voltage level, the power detector allows the device to enter a bursting phase, and a relatively short duration 915 MHz burst, for example, is generated. In this phase, electrical charge is continuously drawn from Cs, causing the voltage on Cs to decrease. The power detector shuts off the burst when the voltage is less than a predetermined low voltage level, and the tagging device re-enters the charging phase to prepare for the next burst. The power level detector may include a hysteretic comparator to monitor the voltage on Cs, and a bias generator to generate a supply-independent reference. The hysteresis window may be determined by way of positive feedback introduced by cross-coupled transistors M2 and M3. A large hysteresis window can be set by establishing a large current-mirror ratio between ratios M1/M2 and M3/M4.

Figure 10:
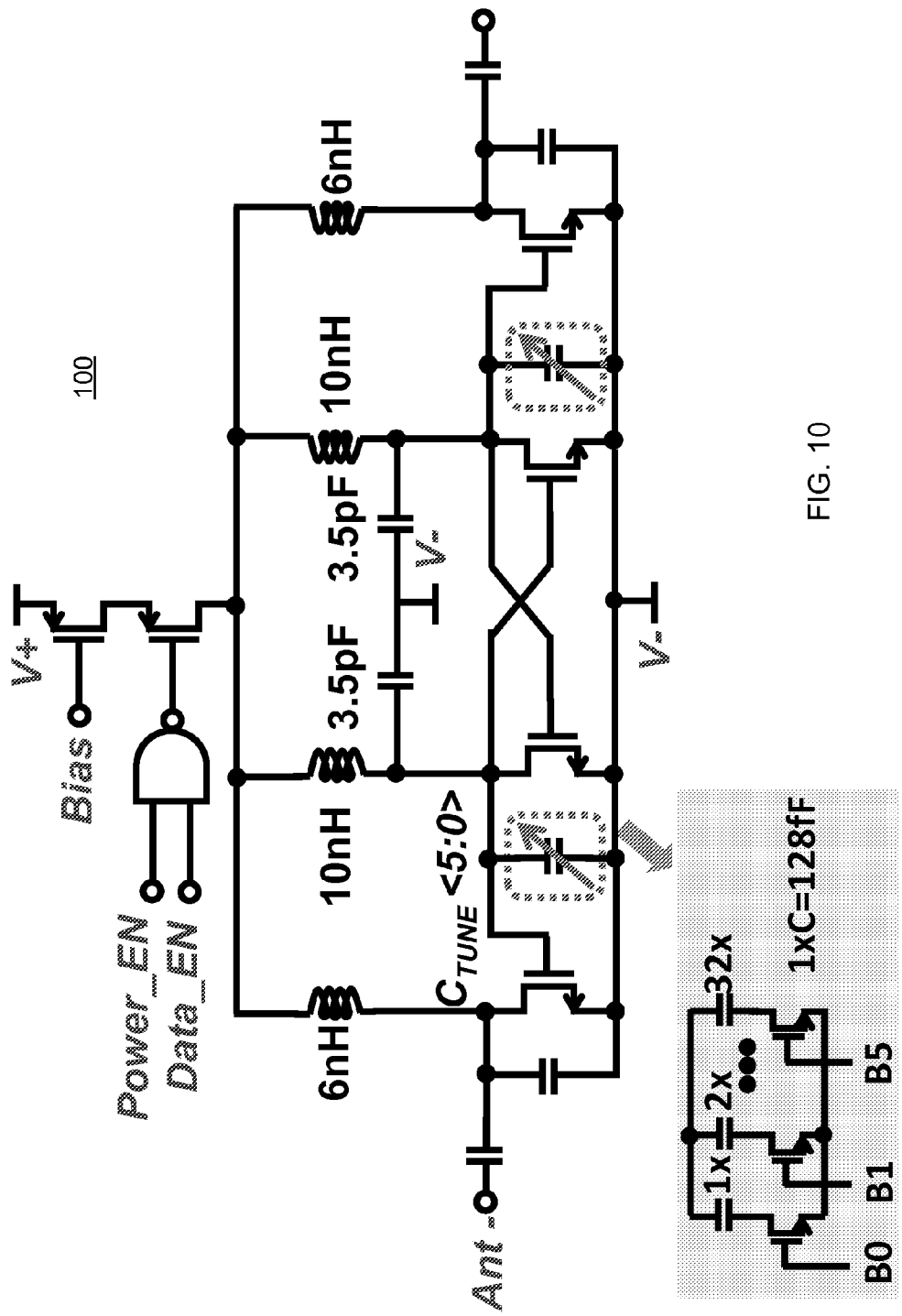
FIG. 10 shows an example of a data modulator as may be used in connection with circuitry embodying aspects of the present invention.

FIG. 10 shows a schematic of an example embodiment of a data modulator 100. In one example embodiment, modulator 100 comprises a voltage controlled oscillator (VCO) followed by a buffer stage to the antenna pads. The VCO is implemented with cross-coupled nMOS pairs to operate under a relatively small voltage headroom. A number of bits (e.g., six bits) of digital control may be used to tune the oscillation frequency from approximately 840 MHz to 937 MHz. The modulator and buffer stage provide approximately −25 dBm of output power (e.g., 50Ω load) when activated. A selectable switch (e.g., pMOS switch) may be used to enable the modulator and generate RF bursts when the voltage on the storage capacitor is larger than 1.5V and the downlink data packet is appropriately received.

Figure 11:
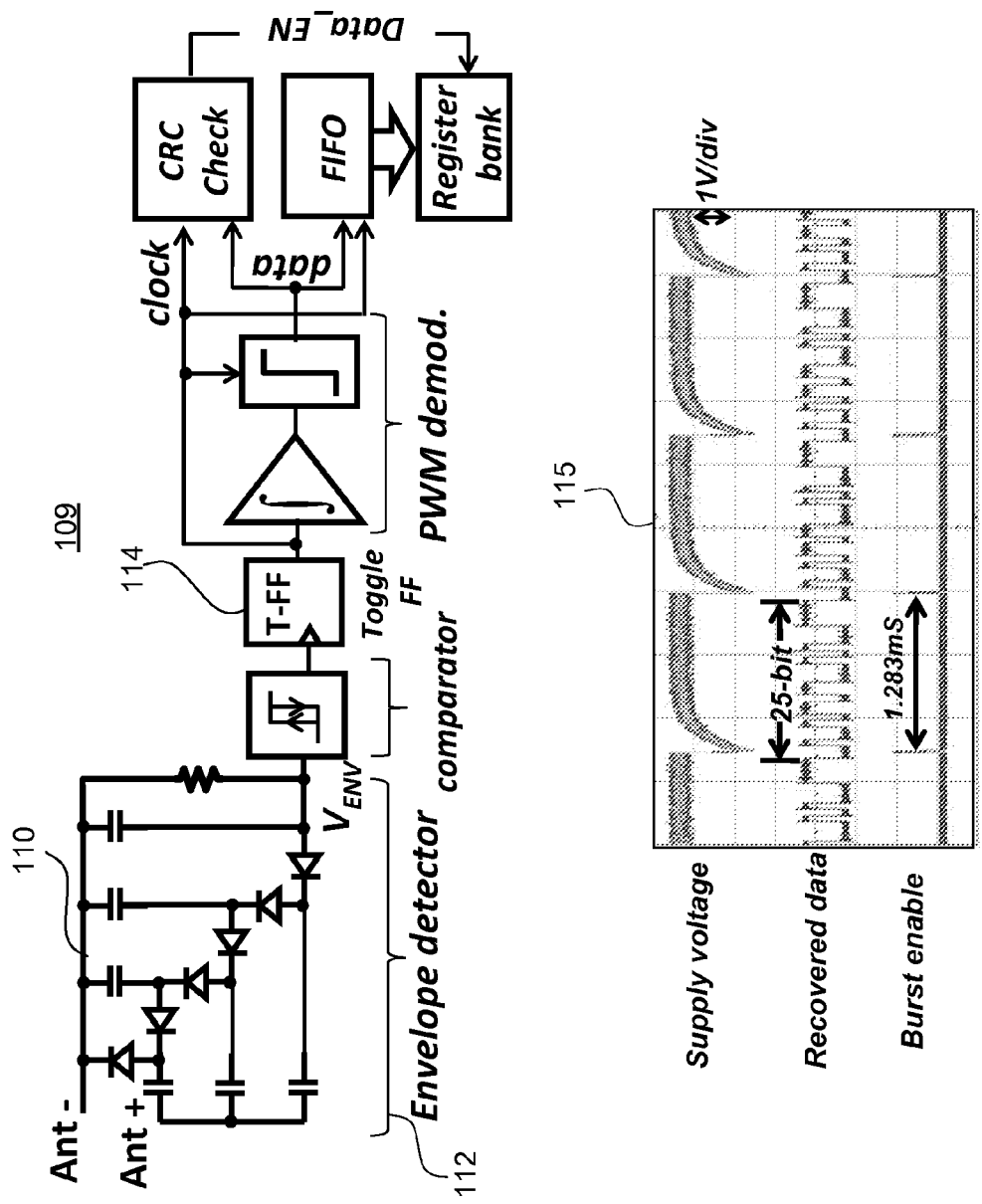
FIG. 11 is a block diagram of an example receiver stage embodying aspects of the present invention and including example waveforms in connection with the receiver stage.

FIG. 11 is a block diagram of an example receiver stage 109. An example RF rectifier that may be used to convert an AC signal extracted at the input port into a DC voltage may be an RF-DC multiplier implemented as a diode-multiplier. FIG. 11 illustrates an example full-wave differential RF-DC converter 110 with N stages (in this example N=3) driven through the low frequency powering channel. Each stage may include two half-wave voltage doublers, one connected to capture positive cycles of a sinusoidal input voltage Vin and the other one connected to capture negative cycles of the sinusoidal input voltage Vin. Thus, each stage results in an ideal 4× boost of the amplitude (twice the peak-to-peak value). If the multiplier is composed of ideal diodes and operating with infinite load, the generated DC voltage Vout will eventually reach 4 NVin. It will be appreciated, however, that in practice due to the finite diode turn-on voltage and reverse charge leakage of practical diodes, Vout is smaller than the ideal case by at least 4 N times the diode turn-on voltage. The presence of static current consumption, Is, counteracts the charging mechanism and loads the diode-multiplier, leading to a further decrease in the steady-state output voltage.

An envelope detector 112 and a clock-data recovery module are used to demodulate data packets, such as may be composed of 20 bits and 1.315 ms in total duration. A pulse width modulation (PWM) scheme may be used to encode data with gaps between pulses of approximately 3.25 μs. As previously discussed, a 3-stage RF-DC converter 110 is used to extract the envelope which is compared against a low-pass filtered reference to generate the recovered pulses, and subsequently converted to pulse-width modulated (PWM) data using a toggle register 114. Since the pulses may occur at approximately 30% or 70% of the bit-time duration, the full-rate (non-return-to-zero) clock edge information is readily available. A NRZ data stream may be recovered by integrating the PWM waveform with a charge pump circuit, and sampling the analog waveform with a latched comparator. FIG. 11 further illustrates example waveforms 115 in connection with receiver stage 109.

Supply Modulated Tag

Figure 12:
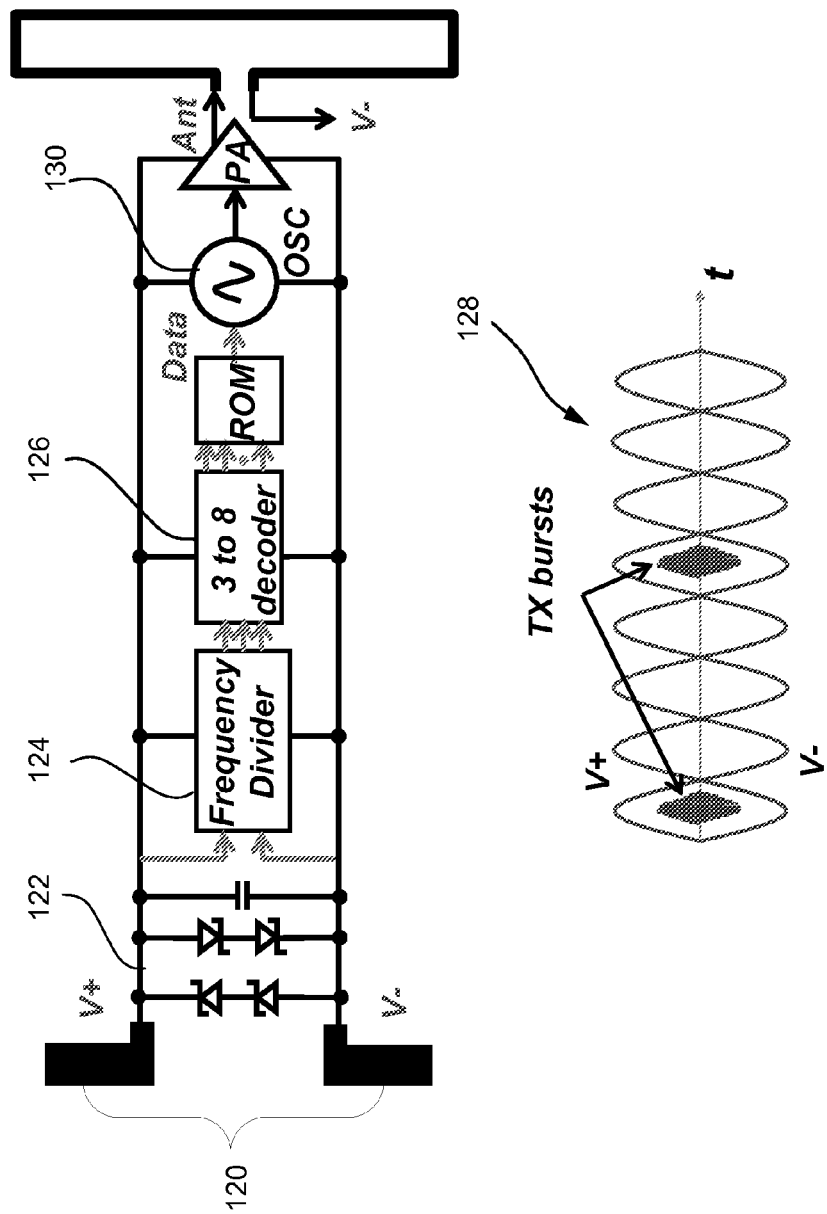
FIG. 12 shows another example embodiment of RF tag topology, which eliminates the need of an RF-DC converter stage and including example waveforms indicative of transmission burst transmitted by the device.

FIG. 12 shows an example RF tag topology which eliminates the need of an RF-DC converter stage. This topology employs direct coupled circuitry powered from relatively low frequency AC signals (e.g., 100 KHz) using a modulated (varying) supply voltage. When the differential voltage across low frequency pads 120 reaches approximately 400 mV, the tag generates RF bursts at approximately 900 MHz with a periodicity determined by the frequency of the applied AC signal. See for example waveforms 128 representative of transmission bursts transmitted by the device. The supply modulator tag comprises an input RF limiter 122, a frequency divider 124, an AC logic decoder 126, a ROM 128 and a ring-oscillator 130 followed by a power amplifier PA. The RF limiter may be used to provide coarse regulation of the supply voltage which is activated once the differential voltage exceeds 400 mV. The divider is used to generate a low frequency clock from the supply modulating AC signal to synchronize internal tokens to the external AC clock. An AC logic decoder may be used to process an internal identification word stored within the ROM, which is fed to the modulator to transmit the corresponding message via the power amplifier. It will be appreciated that the tagging electronic functions may be synchronized with an external reader via a clock signal extracted from a power carrier. This clock can be fed to an on-board phase-lock-loop (PLL) to synchronize phase and frequency of a transmitted carrier. The PLL along with the power amplifier can be activated only during bursting operations to decrease power requirements.

Figure 13:
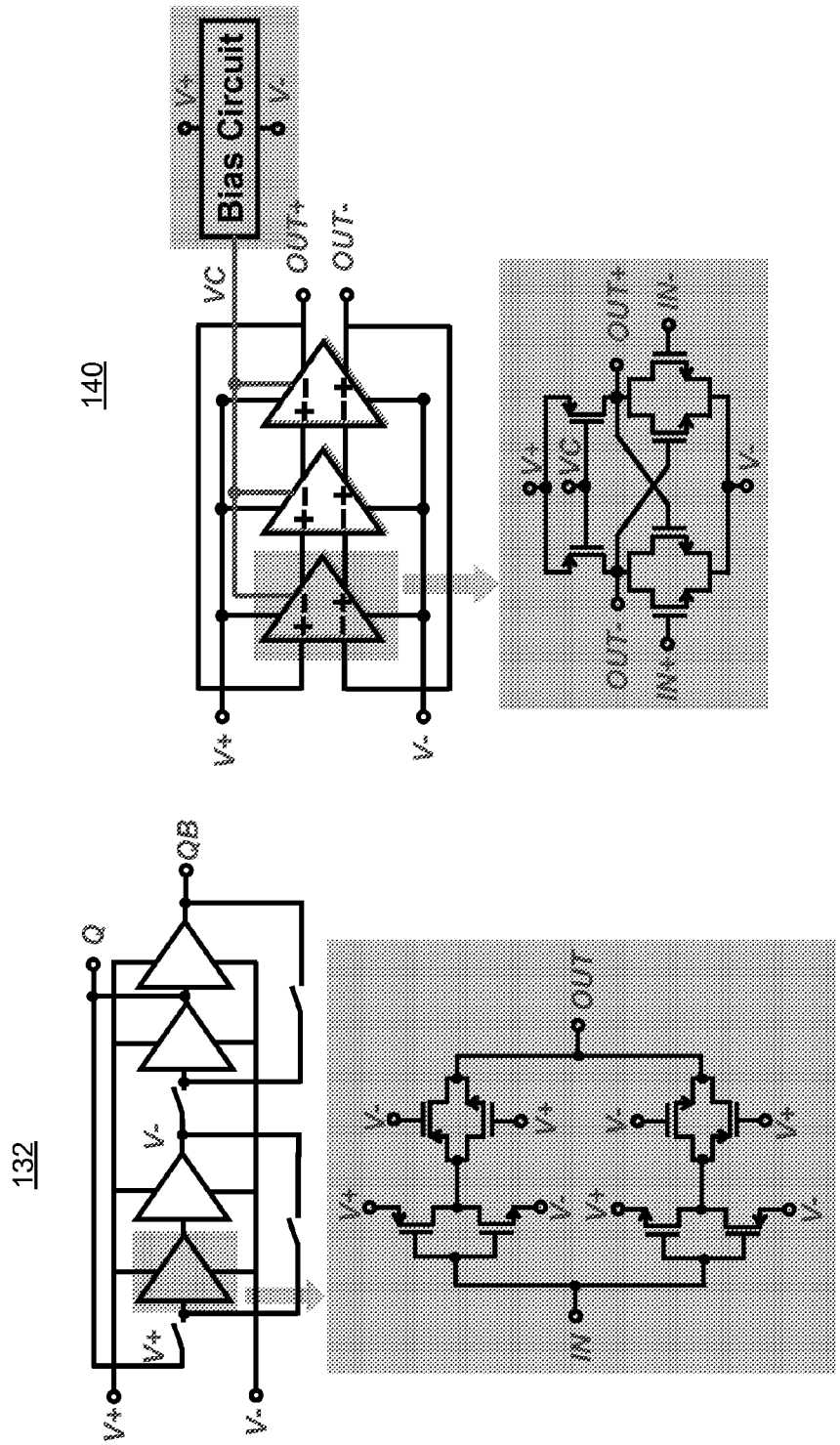
FIG. 13A shows an example of AC logic latch as may used in connection with circuitry embodying aspects of the present invention.
FIG. 13B shows an example of a 3-stage ring oscillator as may be used in connection with circuitry embodying aspects of the present invention.

FIG. 13A shows an example of AC logic latch 132. The AC logic comprises two signal paths, one activated when the voltage induced across the supply is positive, and the second one when the voltage induced is negative. Each path may include a standard CMOS logic gate followed by a transmission gate to enable or disable the signal path. The AC logic evaluates the corresponding logic function by appropriately selecting each path during both negative and positive supply voltage excursions. FIG. 13B shows an example embodiment of a 3-stage ring oscillator 140 and a corresponding delay cell which operates for both negative and positive supply voltages. A bias circuit detects the potential difference across the supply and adjusts the bias current in the delay cells to compensate for supply voltage delay dependence.

Figure 14:
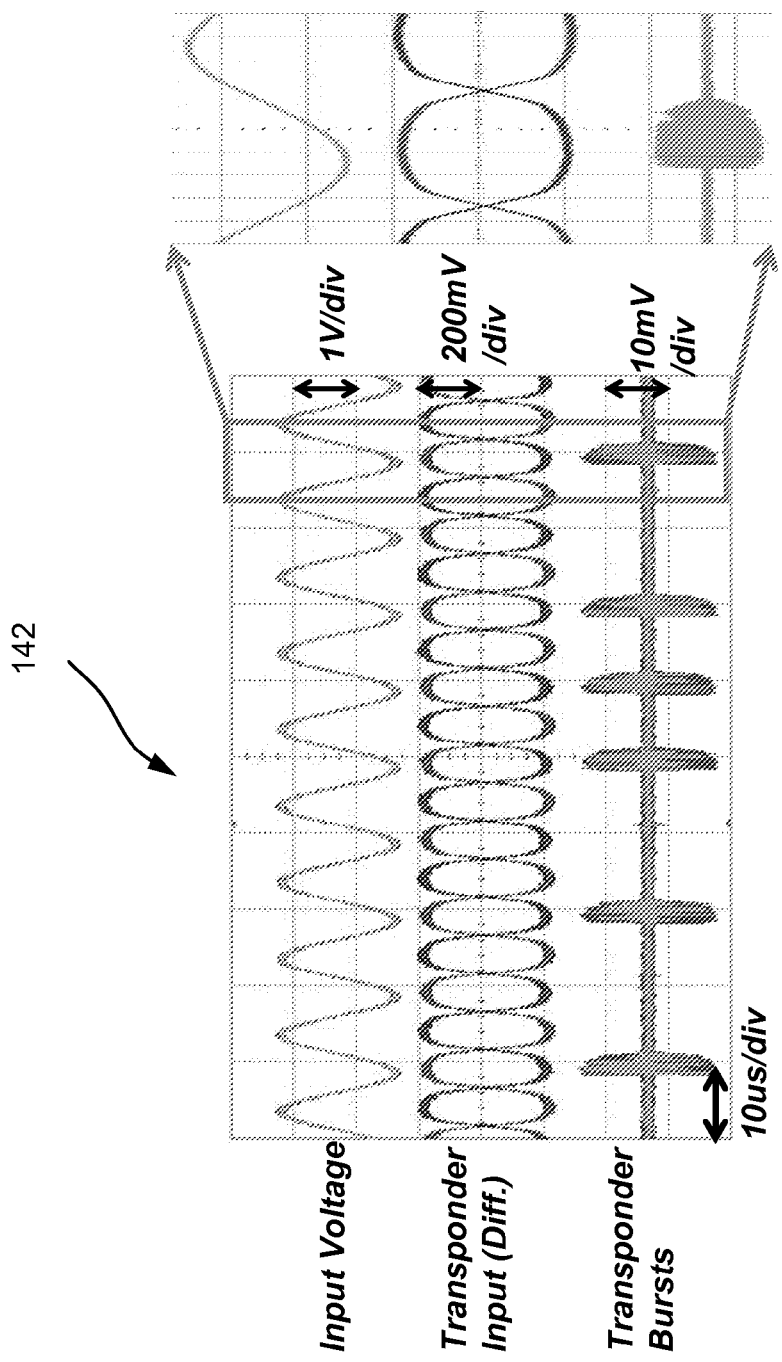
FIG. 14 shows example timing waveforms for a supply modulated tag embodying aspects of the present invention.

FIG. 14 shows example timing waveforms 142 for a supply modulated tag. The tag transmits a predetermined message by generating a burst when the supply voltage reaches an appropriate differential voltage to activate the internal circuits. The presence of a burst may indicate a "1" bit transmission whereas the absence of a burst may indicate a "0" bit transmission.

Capsule Antennas

Radio frequency signal propagation inside the human body has been studied extensively. See for example: C. Gabriel, S. Gabriel and E. Corthout: "The dielectric properties of biological tissues: I. Literature survey", Phys. Med. Biol. v. 41, pp. 2231-2249, 1996. In order to capture the interactions of radiating elements inside the body, we have evaluated the field distributions of electrically small antennas in various FCC regulated frequency bands using the finite difference time domain (FDTD) method and a complete electrical model of an average American male with 23 different tissue types. Simulations were carried out to calibrate the results against theoretical benchmarks of well characterized loop and dipole antennas, and included determining the appropriate mesh size, cell size, time steps, radiation boundaries, padding cells and source type to yield convergence within a reasonable time.

Figure 15:
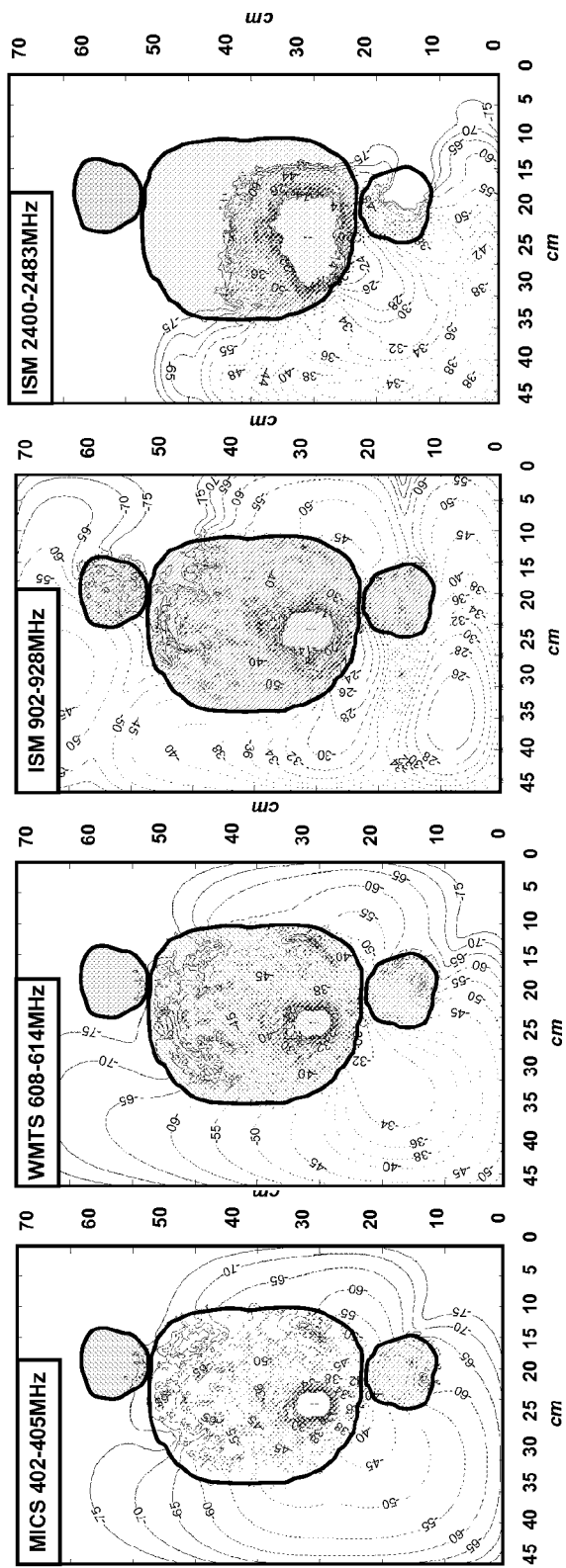
FIG. 15 shows simulated field distributions of an example antenna placed in-body for various regulated frequency bands.

Field distributions of an electrically small dipole antenna placed in the stomach were simulated in various FCC regulated frequency bands to determine a suitable operating frequency for the RF transponder. A miniaturized zigzag antenna, such as shown in FIG. 2, may have a measured return loss of −14.4 dB at 5.78 GHz and in one example case such an antenna was used in the FDTD model to determine the radiation characteristics for a range of FCC regulated frequency bands spanning 400 MHz-2500 MHz. The antenna was placed in the stomach longitudinally (from left to right) slightly off the body axis. For each simulation, the antenna was first designed to resonate at the desired frequencies by forcing a single cell sized gap in the antenna port and inserting a complex source impedance of the appropriate value, which was found via Gaussian source excitation simulations. Near field contour plots in the FCC approved 402 to 405 MHz for Medical Implant Communications Service (MICS) band, 608-614 MHz for Wireless Medical Telemetry Service (WMTS) band, and the 902-928 MHz and 2.4-2.483 GHz for worldwide Industrial-Scientific-Medical (ISM) bands are shown on FIG. 15.

Simulation results that were performed show that the radiated field intensity of the capsule antenna, assuming input power of 0 dBm, is strongest in the anterior location slightly to the left of the stomach for 915 MHz band. It is noted that despite the increasing absorption of electromagnetic energy at frequencies above 1 GHz due to increased water content, the radiation field intensity at the 2.4 GHz ISM band is comparable to that of the 915 MHz ISM band; this is largely due to improved radiation efficiency of the zig-zag dipole antenna at higher frequencies.

Figure 17:
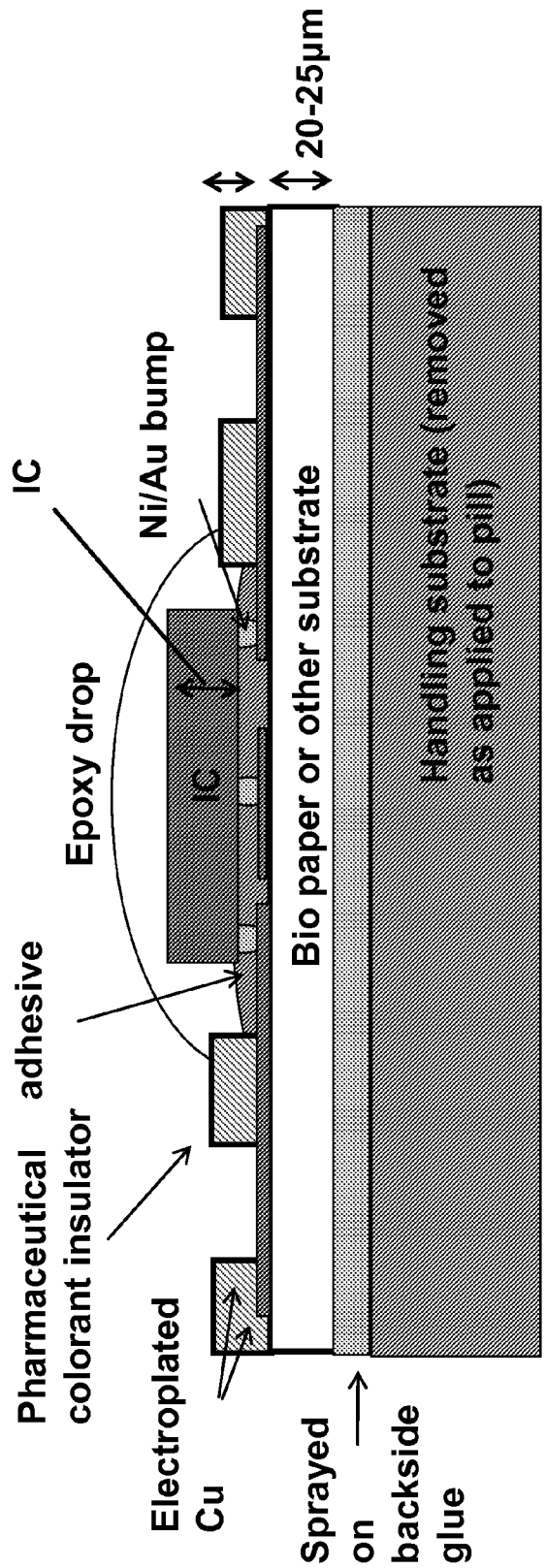
FIG. 17 shows a cross-sectional view of a possible RF tag assembly embodying aspects of the present invention.
Figure 18:
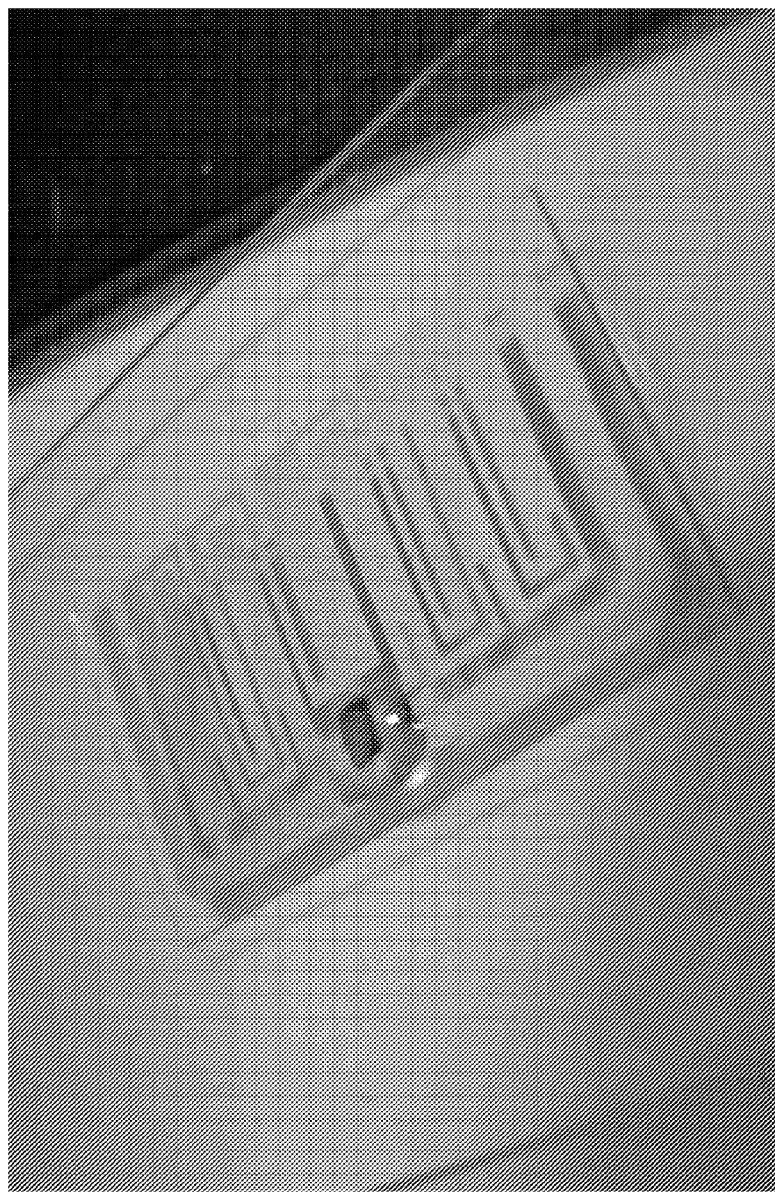
FIG. 18 shows a generally isometric view of an RF tag embodying aspects of the present invention.

FIG. 16 shows an example embodiment of a 915 MHz antenna designed to wrap around a capsule. Input impedance measurements show resonance around the desired 915 MHz ISM band for high frequency RF transmission, shown to be optimal in one embodiment of the design. FDTD simulations show maximum field strength radiation in anterior of the body location slightly to the left of the stomach Tag Assembly and Measurements In order to experimentally verify the inventions, prototypes were fabricated in 130 nm CMOS and assembled into a tag. One possible cross-section of a tag assembly is shown in FIG. 17. The tag can be assembled on a biocompatible substrate which can be made to dissolve. Inks can be applied to the substrate using a variety of printed methods such as screen printing, electroplating, etc, or other methods compatible with large scale manufacturing of tags. Chip attachment to the tag inlay can be accomplished using standard flip-chip attachment techniques. The chip can be covered using a protective coating such as biocompatible epoxy. FIG. 18 shows an example finish tag.

The tags were validated using phantom solutions. Phantoms are solutions that exhibit electrical properties that are approximately equivalent to biological tissue and are used herein to evaluate the E-burst device performance. While phantom preparations vary in complexity and accuracy, the simplest formulation, which has been used in our experiments, is based on sodium chloride (NaCl) and distilled water, however, improved gel based phantoms consisting of polysaccharide gel, NaCl, aluminum powder and Sucrose can also be used. In the present experiments, the loading of the phantoms was designed to approximate that of an adult human back to model the torso area. The phantom solution was placed in a Rubbermaid container measuring 40×40×25 cm$^3$. The relative concentrations of NaCl in roughly 4 liters of distilled water were varied until the loading of an external surface coil in proximity to an adult human back was approximately equal to the loading generated by the sample solution.

Figure 19:
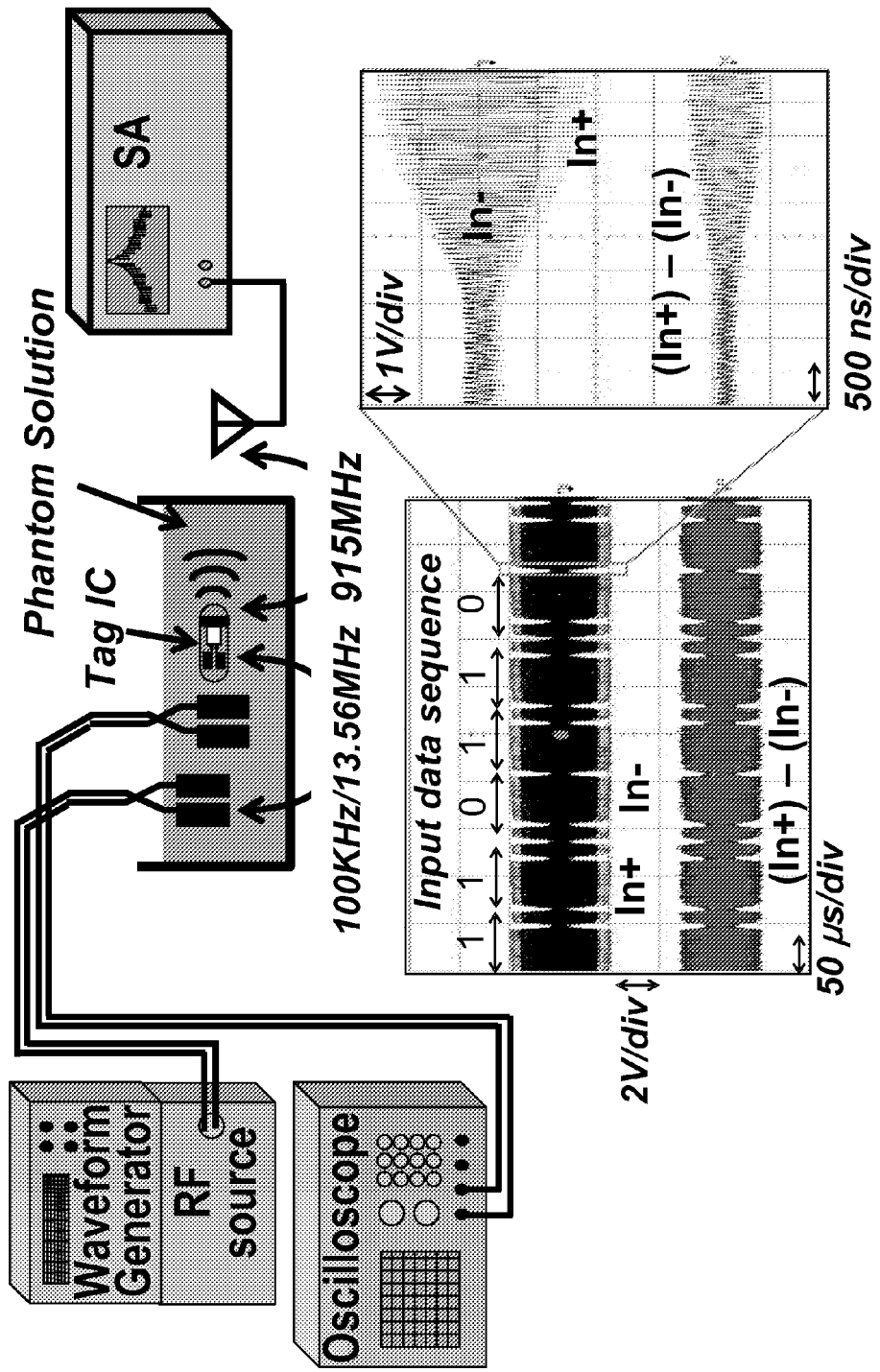
FIG. 19 shows an experimental setup used for measuring characteristics of an RF tag embodying aspects of the present invention.
Figure 20:
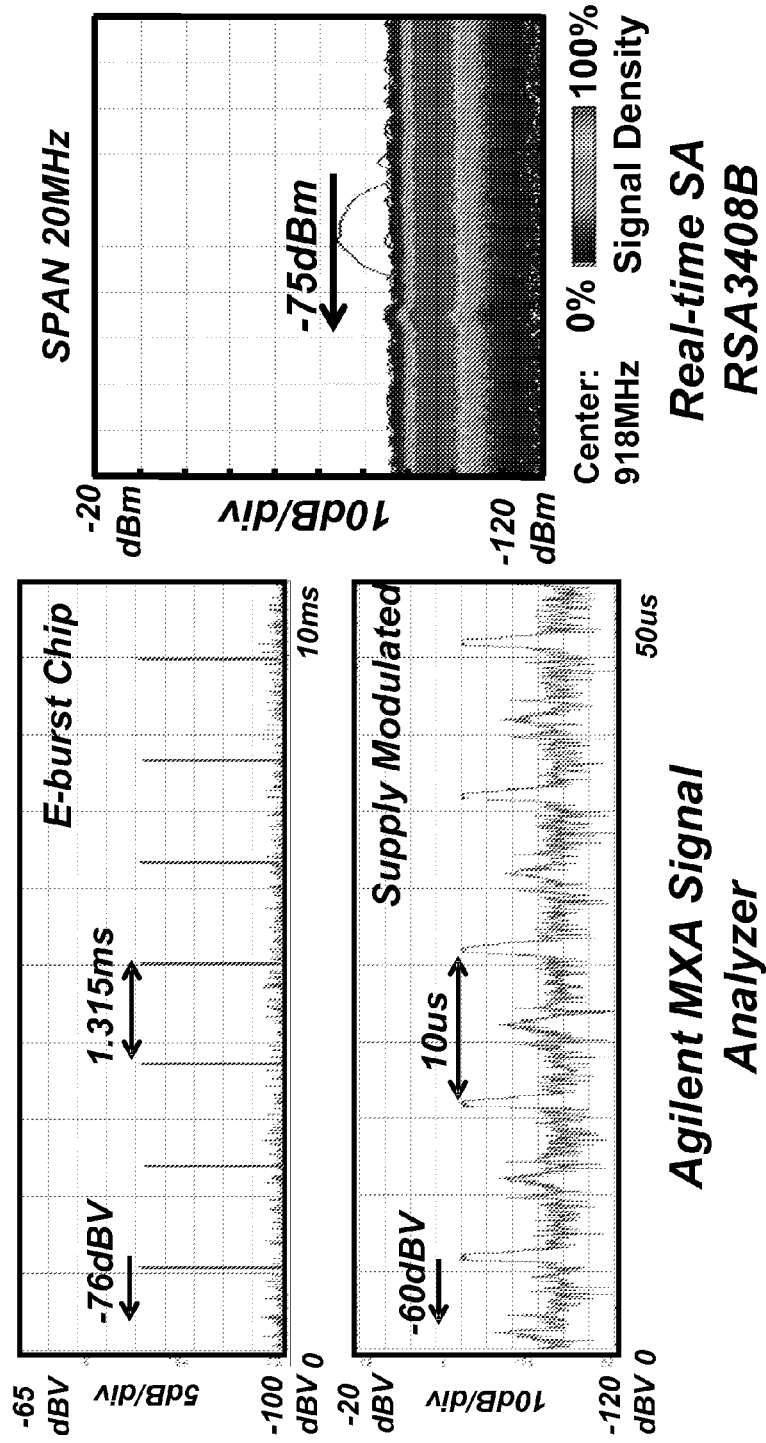
FIG. 20 shows example waveforms including RF bursts generated by devices embodying aspects of the present invention from a phantom solution as captured by a vector signal analyzer with a built-in demodulation function.
Figure 21:
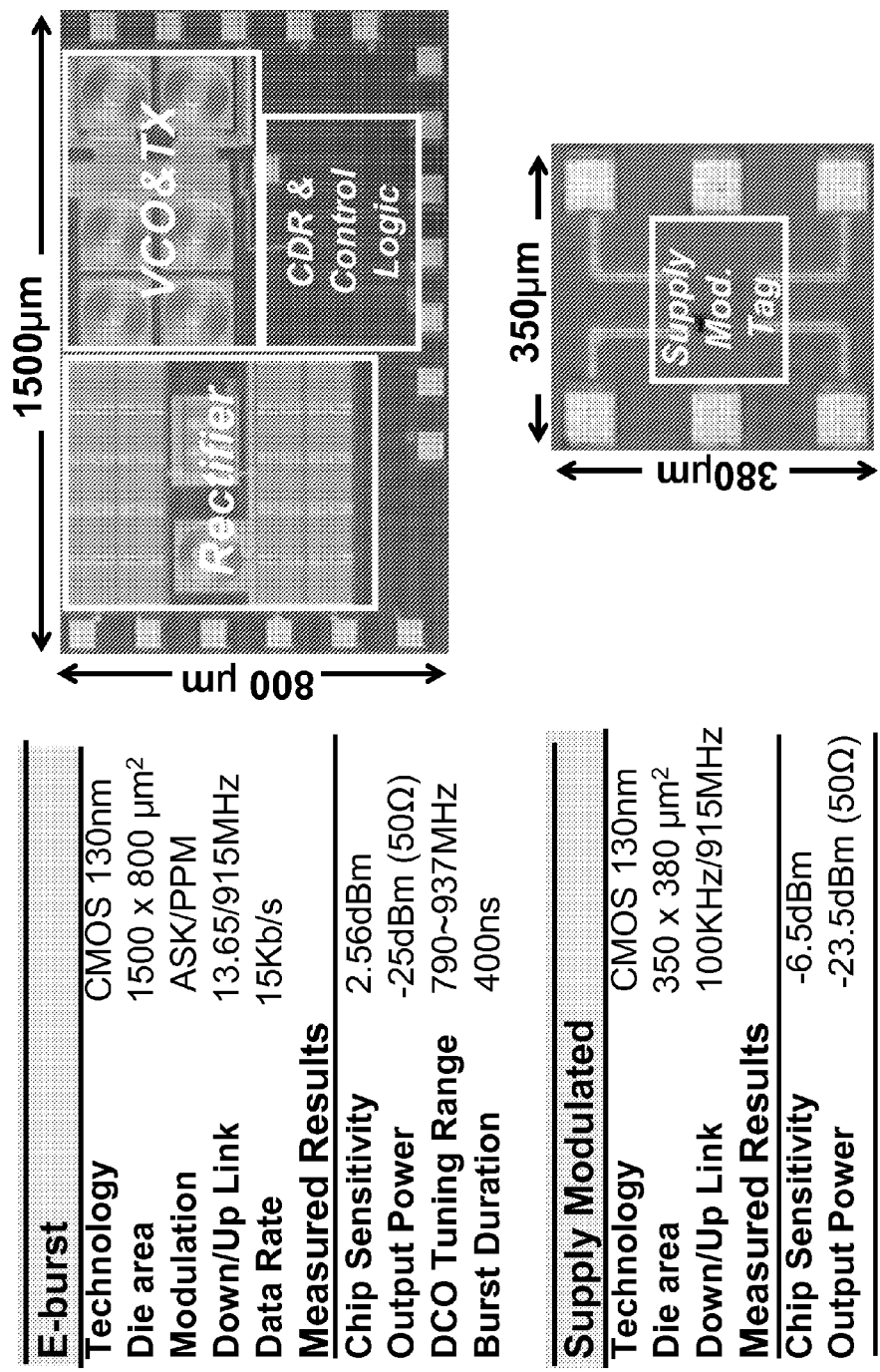
FIG. 21 shows die photos and sample performance of respective devices embodying aspects of the present invention.

The experimental setup and measured results are shown in FIG. 19. A low frequency RF source is used to activate the E-burst chip inside the phantom solution. Low frequency transmit pads are applied directly into the phantom solution. The modulated AC signal is verified using a second set of low frequency pads connected to two independent channels in an oscilloscope. While the voltages generated in each probe, labeled In+ and In−, are nearly in phase, a sufficiently large differential voltage (In+−In−) is induced across the probes to power the tag. As shown in FIG. 20, RF bursts generated by the prototype E-burst and supply modulated microchips from inside of the phantom solution were captured by a vector signal analyzer with a built-in demodulation function (Agilent N9020A). The receiving antenna was placed outside of the phantom container, and the prototype device was immersed in the center of the phantom solution (~20 cm from the sidewalls). A periodic downlink data packet activates the transponder at 1.315 ms intervals, generating RF bursts of approximately 400 ns in duration and a measured signal level of −76 dBV (at the receiving antenna). The supply modulated tag generates detectable levels of −60 dBV at 10 µs intervals. FIG. 21 shows die photos and a performance summary of the E-burst and supply modulated tag.

An E-burst and Supply Modulated RF capsule tagging system is proposed for medication capsule monitoring. The RF tag utilizes a galvanic powering scheme and communication protocol to circumvent problems associated with signal attenuation inside the human body and poor radiation efficiency of electrically small antennas. Since the power levels required to activate a tag are orders of magnitude larger than what is detectable externally, we employ an asymmetric RF link to energize the transponder at low frequency and transmit RF bursts at higher frequencies.

What is claimed is:

1. A miniaturized in-body electronic device comprising:
at least one dipole antenna configured to receive an AC signal sent via galvanic coupling through a body of a subject when the in-body electronic device is located therein, and also configured as oxidizing and reduction electrodes of an electrochemical battery when the in-body electronic device is exposed to internal gastric acid;
power extraction circuitry configured to extract electrical power from the at least one dipole antenna, the extracted electrical power being accumulated over a charging cycle;
a transmitter coupled to receive power from the power extraction circuitry; and
a controller coupled to the transmitter, wherein the controller is configured to activate the transmitter to generate a sequence of intermittent transmission bursts for transmitting an uplink signal.

2. The in-body electronic device of claim 1, wherein the power extraction circuitry comprises an AC-to-DC converter and an energy storage device coupled to receive a DC signal from the AC-to-DC converter.

3. The in-body electronic device of claim 2, wherein the power extraction circuitry further comprises a power level detector coupled to the energy storage device, the power level detector coupled to provide a signal to the controller indicative of an electrical charge status of the energy storage device.

4. The in-body electronic device of claim 3, wherein the transmission burst occurs during a period of time when the charge status of the energy storage device meets or exceeds a charge threshold value.

5. The in-body electronic device of claim 1, wherein the power extraction circuitry is configured to power the transmitter from an AC power input without an AC to DC converter.

6. The in-body electronic device of claim 5, wherein a periodicity of the sequence of intermittent transmission bursts is determined by the frequency of the AC signal sent via galvanic coupling.

7. The electronic device of claim 1, wherein a transmission of the uplink signal occurs contemporaneously with a reception of the AC signal sent via galvanic coupling.

8. The electronic device of claim 1, wherein a transmission of the uplink signal is temporally spaced relative to a time of reception of the AC signal sent via galvanic coupling.

9. The electronic device of claim 1 further comprising at least a second antenna coupled to the transmitter to transmit the uplink signal.

10. The electronic device of claim 1, wherein the uplink signal comprises a frequency higher than that of a downlink signal in response to receipt of which the controller is configured to direct transmission of the uplink signal.

11. The in-body electronic device of claim 1, wherein said device comprises a semiconductor chip and said at least one dipole antenna is embedded in the chip.

12. The in-body electronic device of claim 1, wherein the power level of the burst is higher than power instantaneously available from said at least one dipole antenna.

* * * * *